(12) United States Patent
Yarita

(10) Patent No.: US 8,437,820 B2
(45) Date of Patent: May 7, 2013

(54) SIGNAL PROCESSING METHOD, SIGNAL PROCESSING APPARATUS, AND PULSE PHOTOMETER USING THE SAME

(75) Inventor: Masaru Yarita, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 992 days.

(21) Appl. No.: 12/427,623

(22) Filed: Apr. 21, 2009

(65) Prior Publication Data

US 2009/0264721 A1     Oct. 22, 2009

(30) Foreign Application Priority Data

Apr. 22, 2008 (JP) .................................. 2008-111391
Apr. 22, 2008 (JP) .................................. 2008-111392
Oct. 21, 2008 (JP) .................................. 2008-270730

(51) Int. Cl.
*A61B 5/00* (2006.01)

(52) U.S. Cl.
USPC ......................................................... 600/310

(58) Field of Classification Search .................. 600/309, 600/310, 322, 323, 326, 328–330
See application file for complete search history.

(56) References Cited

FOREIGN PATENT DOCUMENTS

JP         3270917 P       4/2002
JP         2003-135434 A   5/2003

*Primary Examiner* — Brian Szmal
(74) *Attorney, Agent, or Firm* — Kenealy Vaidya LLP

(57) ABSTRACT

A method of processing first and second signals obtained by measuring a medium, to obtain a pulse wave signal and an artifact signal which are separated, includes: separating vectors of the first and second signals by using a separation matrix into a vector of the pulse wave signal and a vector of the artifact signal, the separation matrix including a norm ratio of a stable zone of the pulse wave signal and a compensated norm ratio of an artifact zone.

6 Claims, 18 Drawing Sheets

FIG. 6A
FIG. 6B
FIG. 6C
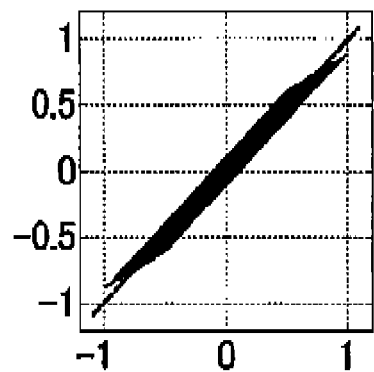
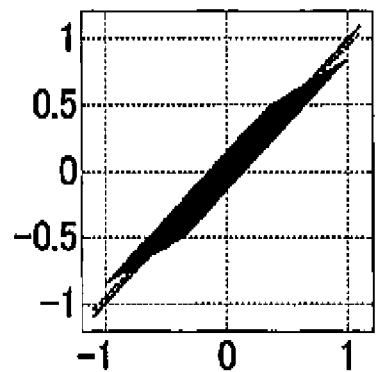
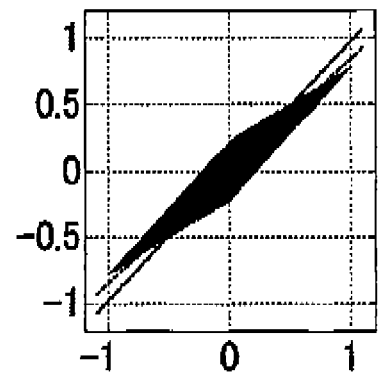
FIG. 7A
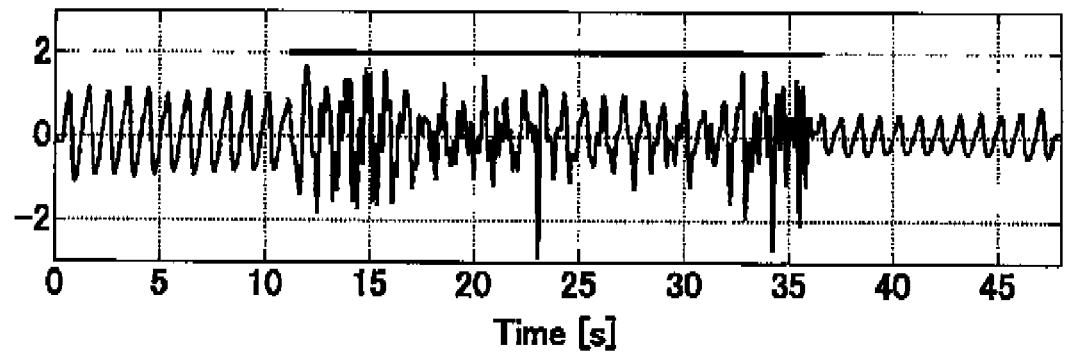
FIG. 7B
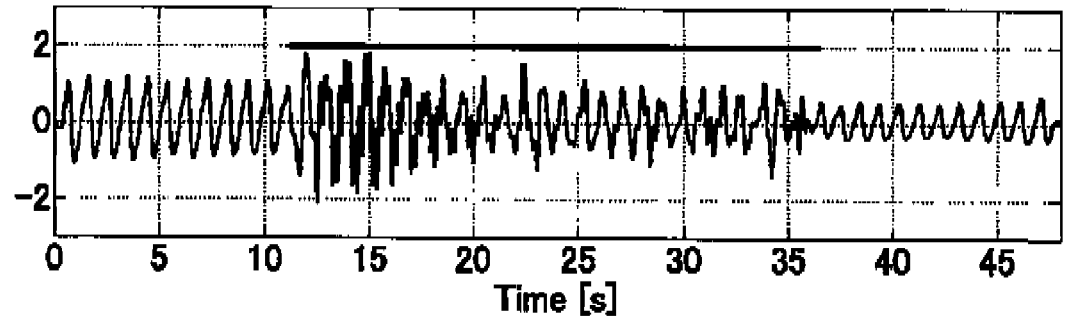

Without compensation

With compensation

Without compensation

With compensation

FIG. 10

|  | H value | |
|---|---|---|
|  | 0.5-5 Hz filter | Filter +smoothed (17) |
| $\emptyset_N = 0.6703$ | 0.3388 | 0.2765 |
| $\emptyset_N^+ = 0.7099$ | 0.0042 | 0.0492 |

| type | A ($S\phi_N^+$) | B ($\phi_N^+$) | C ($\phi_N$) |
|---|---|---|---|
| $H$ value | 0.0187 | 0.0521 | 0.2023 |

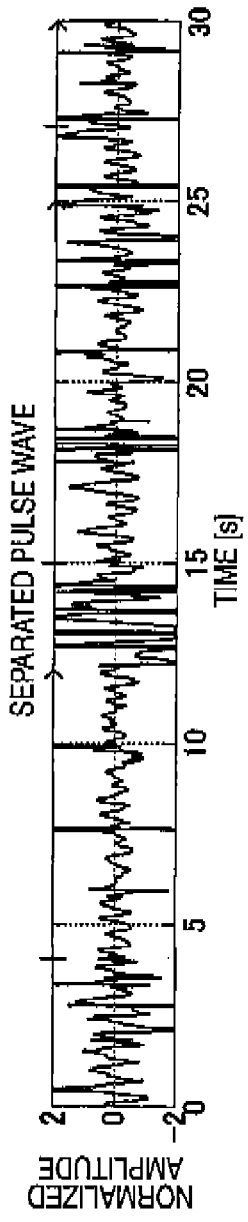
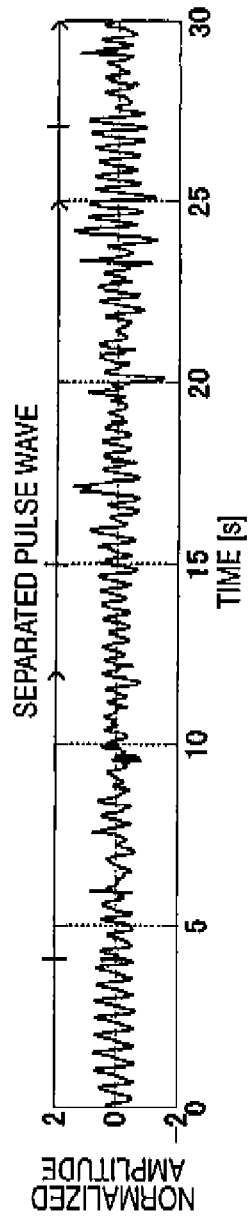
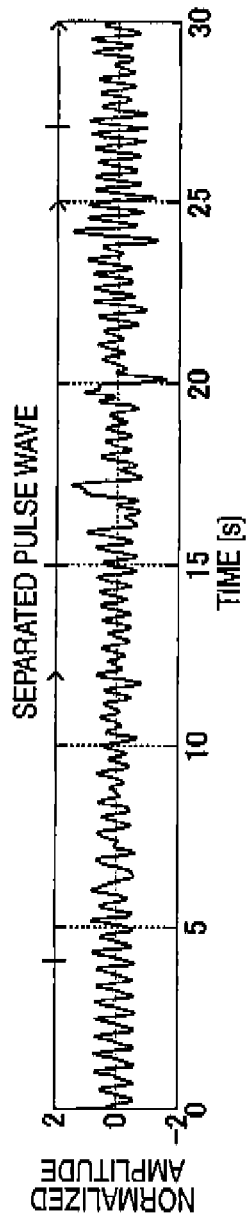
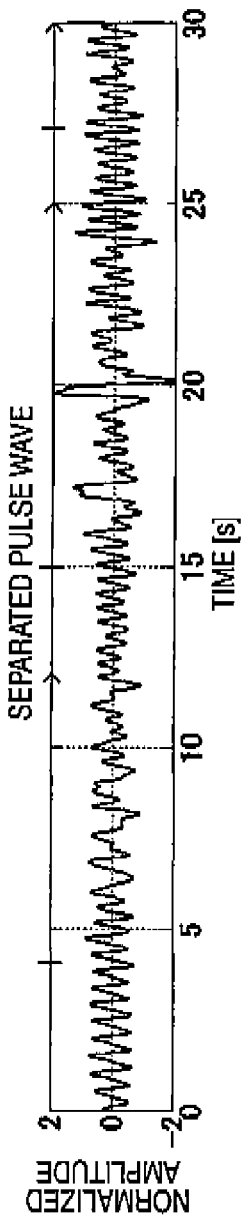
FIG. 18A
FIG. 18B
FIG. 18C
FIG. 18D

SIGNAL PROCESSING METHOD, SIGNAL PROCESSING APPARATUS, AND PULSE PHOTOMETER USING THE SAME

BACKGROUND OF THE INVENTION

The present invention relates to signal processing where a common signal component is extracted by processing two homogeneous signals which are extracted substantially simultaneously from one medium and, and more particularly to an improvement of signal processing in a pulse photometer which is used in the medical field, particularly in the diagnosis of the circulatory system.

As a method of separating signal and noise components from two signals which are extracted substantially simultaneously from one medium, various methods have been proposed.

The methods are performed through frequency domain processing and time domain processing.

Also in medical practice, for example, a so-called photoplethysmograph which measures a pulse waveform and a pulse rate, and apparatuses for measuring the concentration of a light-absorbing material contained in the blood, such as an apparatus for measuring the oxygen saturation SpO2, that for measuring the concentration of dyshemoglobin such as carboxyhemoglobin or methemoglobin, and that for measuring the dye concentration injected in the blood are known as a pulse photometer.

Among such apparatuses, an apparatus for measuring the oxygen saturation SpO2 is called a pulse oximeter.

A pulse photometer operates on the following principle. Light beams of plural wavelengths which are different in light absorbency to the target substance are transmitted through or reflected from living tissue, the intensity of reflected or transmitted light is continuously measured, and the concentration of the target substance is obtained from a pulse wave data signal obtained in the measurement.

When noises are mixed into the pulse wave data signal, there is the possibility that the concentration cannot be correctly calculated and erroneous treatment may be caused.

In order to reduce the noise level in a pulse photometer, methods such as that where the frequency band is divided and attention is paid on signal components, and that where a correlation between two signals is determined have been proposed. However, the methods have a problem that the analysis requires a prolonged time period.

Therefore, the assignee of the present invention has proposed an art in Japanese Patent No. 3,270,917 where light beams having two different wavelengths impinge on living tissue, two pulse wave signals are obtained from transmitted light beams, a graph is formed while using the level of the two pulse wave signals as the ordinate and abscissa, respectively to obtain a regression line, and the oxygen saturation of arterial blood or the concentration of a light-absorbing material is obtained on the basis of the gradient of the regression line. According to the related art, the measurement accuracy is improved, and the power consumption is reduced. In order to obtain a regression line or the gradient thereof by using many sampling data with respect to pulse wave signals of the wavelengths, however, a large computation processing power is required.

Furthermore, the assignee of the present invention has proposed a method in JP-A-2003-135434 where, although a frequency analysis is used, a pulse wave signal itself is not extracted in the analysis unlike a related art, but fundamental frequency of the pulse wave signal, and the pulse wave signal is filtered by using a filter using harmonic frequencies thereof to enhance the accuracy.

In the use at home, particularly, it is supposed that a pulse oximeter is used in various manners. Therefore, a wide variety of artifacts exist, and a higher anti-artifact property is requested in the case of SpO2 which is used in a hospital.

When an artifact is contained, the measurement system is disturbed, and there is a case where SpO2 is erroneously displayed.

A typical artifact is body motion. For example, such an artifact is caused by a phenomenon where a probe which is attached to the subject to be measured is moved by body motion, and the optical path between the light source and a light-receiving face is changed, or living tissue is deformed by a force applied to the tissue.

In the case of a neonatal infant or an infant child, particularly, an artifact is often contained, and a motion of a hand or a foot, bitter sobbing, shiver, cough, and the like function as an artifact source.

SUMMARY

It is therefore an object of the invention to provide a signal processing method, signal processing apparatus, and pulse photometer using the same in which, even in the case where a large artifact such as motion of a hand or a foot, bitter sobbing, shiver, or cough is contained, SpO2 can be measured more correctly.

In order to achieve the object, according to the invention, there is provided a method of processing first and second signals obtained by measuring a medium, to obtain a pulse wave signal and an artifact signal which are separated, the method comprising:

separating vectors of the first and second signals by using a separation matrix into a vector of the pulse wave signal and a vector of the artifact signal, the separation matrix including a norm ratio of a stable zone of the pulse wave signal and a compensated norm ratio of an artifact zone.

The compensated norm ratio may be obtained by the following expression:

$$\overline{\|IR_{pulse}\|}_2 := \frac{\|IR_{pulse}\|_2}{\sqrt{N_{pulse}}}$$

$$\overline{\|IR_{noise}\|}_2 := \frac{\|IR_{noise}\|_2}{\sqrt{N_{noise}}}$$

$$\overline{\|R_{pulse}\|}_2 := \frac{\|R_{pulse}\|_2}{\sqrt{N_{pulse}}}$$

$$\overline{\|R_{noise}\|}_2 := \frac{\|R_{noise}\|_2}{\sqrt{N_{noise}}}$$

$$\phi_N^+ = \sqrt{\left|\frac{(\overline{\|R_{noise}\|}_2)^2 - (\overline{\|R_{pulse}\|}_2)^2}{(\overline{\|IR_{noise}\|}_2)^2 - (\overline{\|IR_{pulse}\|}_2)^2}\right|}$$

where $$(\overline{\|IR_{noise}\|}_2)^2 \ne (\overline{\|IR_{pulse}\|}_2)^2$$

A moving average process with a predetermined number of points may be performed on the pulse wave signal.

In order to achieve the object, according to the invention, there is also provided a biological signal processing apparatus comprising:

a measuring unit measuring the first and second signals; and a processing unit processing the first and second signals by using the above method.

In order to achieve the object, according to the invention, there is also provided a pulse photometer including the biological signal processing apparatus according to claim 4, and calculating at least one of an oxygen saturation of arterial blood, a dyshemoglobin concentration, and dye concentration injected in the blood, wherein the first and second signals are electric signals into which lights obtained by causing two kinds of light beams, which are emitted from a light emitter and which have different wavelengths, to be transmitted through or reflected from living tissue corresponding to the medium are converted, and wherein a component of the artifact signal is removed by using the compensated norm ratio to obtain the pulse wave signal.

In order to achieve the object, according to the invention, there is also provided a method of processing first and second signals obtained by measuring a medium, to obtain a pulse wave signal and an artifact signal which are separated, the method comprising:

separating vectors of the first and second signals by using a separation matrix into a vector of the pulse wave signal and a vector of the artifact signal, the separation matrix including a norm ratio of a stable zone of the pulse wave signal and a successively-compensated norm ratio of an artifact zone.

The successively-compensated norm ratio may be obtained by the following expression:

$$\overline{\|IR_{pulse}\|}_2 := \frac{\|IR_{pulse}\|_2}{\sqrt{N_{pulse}}}$$

$$\overline{\|IR(J)_{J-k:J+k}\|}_2 := \frac{\|IR_{J-k:J+k}\|_2}{\sqrt{2k+1}}$$

$$\overline{\|R_{pulse}\|}_2 := \frac{\|R_{pulse}\|_2}{\sqrt{N_{pulse}}}$$

$$\overline{\|R(J)_{J-k:J+k}\|}_2 := \frac{\|R_{J-k:J+k}\|_2}{\sqrt{2k+1}}$$

$$S\phi_N^+(J) = \sqrt{\left|\frac{(\overline{\|R(J)_{J-k:J+k}\|}_2)^2 - (\overline{\|R_{pulse}\|}_2)^2}{(\overline{\|IR(J)_{J-k:J+k}\|}_2)^2 - (\overline{\|IR_{pulse}\|}_2)^2}\right|}$$

where $$(\overline{\|IR(J)_{J-k:J+k}\|}_2)^2 \neq (\overline{\|IR_{J-k:J+k}\|}_2)^2$$

When the successively-compensated norm ratio satisfies a condition, the successively-compensated norm ratio may be replaced with a prescribed value.

In order to achieve the object, according to the invention, there is also provided a biological signal processing apparatus comprising:

a measuring unit measuring the first and second signals; and a processing unit processing the first and second signals by using the above method.

In order to achieve the object, according to the invention, there is also provided a pulse photometer including the above biological signal processing apparatus, and calculating at least one of an oxygen saturation of arterial blood, a dyshemoglobin concentration, and dye concentration injected in the blood, wherein the first and second signals are electric signals into which lights obtained by causing two kinds of light beams, which are emitted from a light emitter and which have different wavelengths, to be transmitted through or reflected from living tissue corresponding to the medium are converted, and wherein a component of the artifact signal is removed by using the compensated norm ratio to obtain the pulse wave signal.

When the successively-compensated norm ratio satisfies a condition, the successively-compensated norm ratio may be replaced with a value.

BRIEF DESCRIPTION OF THE DRAWINGS

FIGS. 6A, 6B, and 6C are views showing results of three kinds of simulations which were performed while changing relationships between the amplitudes of a pulse wave signal (pulse) and an artifact signal (Artifact).

FIGS. 7A and 7B are views showing a waveform which is obtained by separating an observation signal by a separation matrix S.

FIG. 10 is a view showing results of evaluation of separation of the pulse wave and the artifact by an evaluation function H.

FIGS. 18A to 18D are views showing results of separation in which the pulse wave is separated from the observation waveforms in FIGS. 14A and 14B.

DETAILED DESCRIPTION OF PREFERRED EMBODIMENTS

In the description of an embodiment of the invention, the principle will be described by exemplifying a pulse oximeter which measures the oxygen saturation of arterial blood.

The technique of the invention is not restricted to a pulse oximeter, and can be applied also to an apparatus (pulse photometer) which measures a light-absorbing material contained in the blood such as dyshemoglobin (carboxyhemoglobin, methemoglobin, and the like), and dye injected in the blood, with using the principle of pulse photometry.

Figure 1:
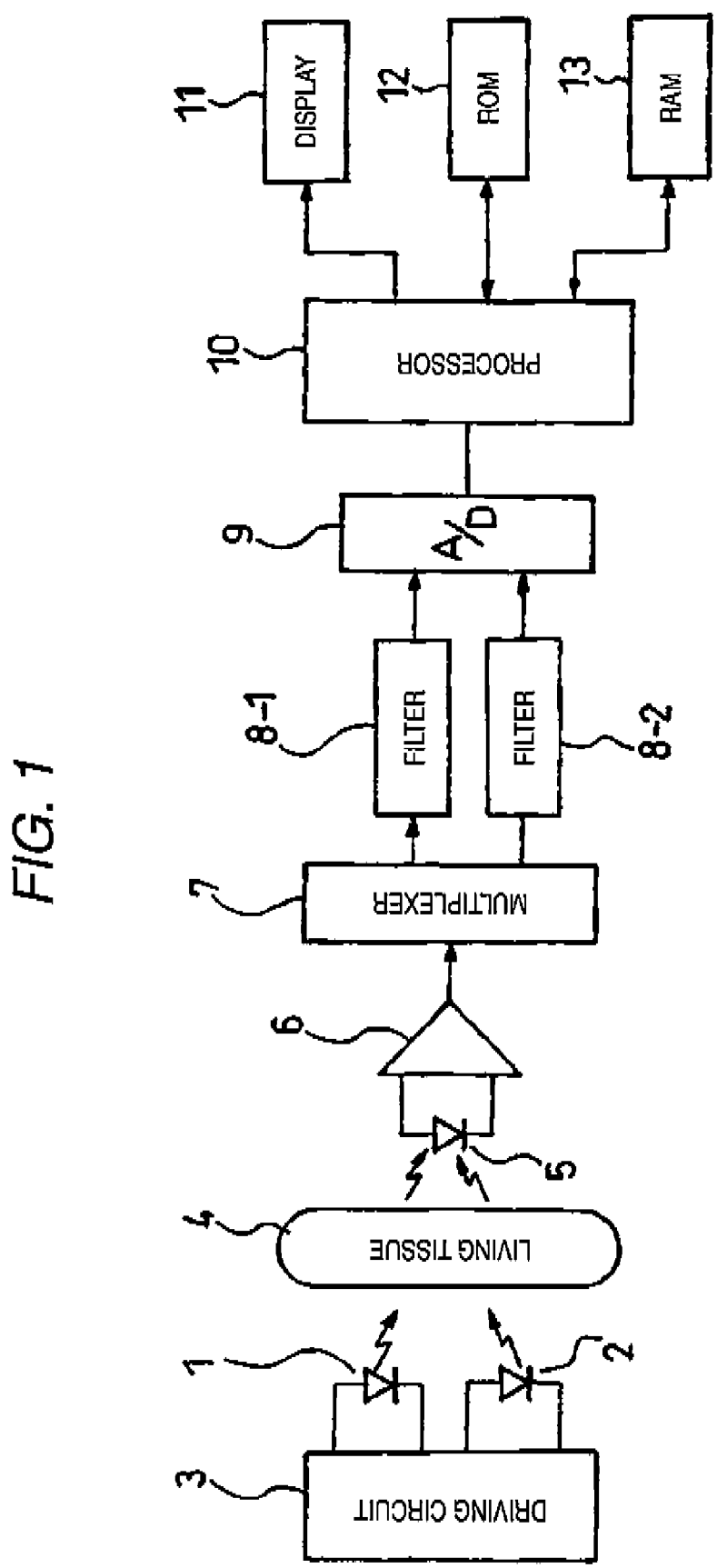
FIG. 1 is a diagram showing the configuration of a pulse oximeter which measures the oxygen saturation of arterial blood.

FIG. 1 which is a schematic block diagram shows the configuration of a pulse oximeter which measures the oxygen saturation of arterial blood.

Photo emitters 1, 2 which respectively emit light beams of different wavelengths are driven by a driving circuit 3 so as to alternately emit the light beams.

Preferably, the light beams emitted from the photo emitters 1, 2 are infrared light (for example, 940 [nm]) which is less affected by the oxygen saturation of arterial blood, and red light (for example, 660 [nm]) which is highly sensitive to a change of the oxygen saturation of arterial blood, respectively.

The light beams emitted from the photo emitters 1, 2 are transmitted through living tissue 4, and then received by a photodiode 5 to be converted into electric signals.

In FIG. 1, the transmitted light beams are received. Alternatively, reflected light beams may be received.

The converted signals are amplified by an amplifier 6, and separately supplied by a multiplexer 7 to filters 8-1, 8-2 respectively corresponding to the light wavelengths.

The signals separately supplied to the filters are filtered by the filters 8-1, 8-2 so that noise components are reduced, and then digitized by an A/D converter 9.

The digitized signal trains corresponding to the infrared light and the red light form the pulse wave signals, respectively.

The digitized signal trains are inputted to a processor 10, and processed by a program stored in a ROM 12. The oxygen saturation SpO2 is measured, and the value of the saturation is displayed on a display 11.

Figure 2A:
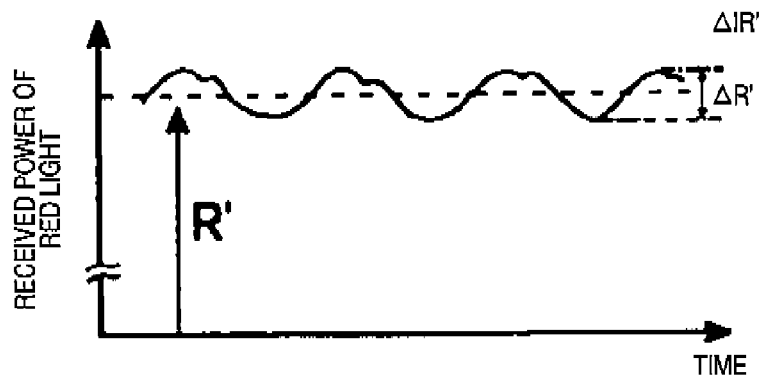
FIGS. 2A and 2B are views showing a measurement example of variations in light absorbance (light attenuation) of a light-absorbing material in blood.
Figure 2B:
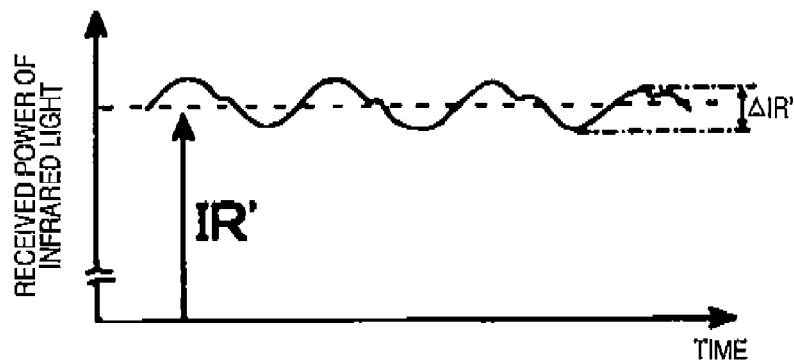

First, measurement of variations in light absorbance (light attenuation) of a light-absorbing material in blood will be described with reference to FIGS. 2A and 2B. FIGS. 2A and 2B show pulse wave data which are obtained by transmitting the light beams emitted from the photo emitters 1, 2 through the living tissue 4, receiving the transmitted light beams on the photodiode 5, and converting the light beams into electric signals. FIG. 2A shows pulse wave data in the case of the red light, and FIG. 2B shows those in the case of the infrared light.

In FIG. 2A, assuming that the abscissa indicates the time and the ordinate indicates the power of received light, the power of light received by the photodiode 5 has a waveform in which the DC component (R') of the red light and the pulsation component (ΔR') are superimposed to each other.

In FIG. 2B, assuming that the abscissa indicates the time and the ordinate indicates the power of received light, the power of light received by the photodiode 5 has a waveform in which the DC component (IR') of the infrared light and the pulsation component (ΔIR') are superimposed to each other.

Each of the measurement waveforms of FIGS. 2A and 2B contains an artifact (noises) due to body motion. There is a frequency band which is common to the frequency component of the artifact and that of the signal. Therefore, it is difficult to correctly obtain the signal component by removing the artifact component.

In the examples of FIGS. 2A and 2B, the degree of the artifact is small. In the following, the description will be made based on an measurement example in which a large artifact corresponding to a large artifact such as a motion of a hand or a foot, bitter sobbing, shiver, cough, or the like is artificially applied.

Figure 3:
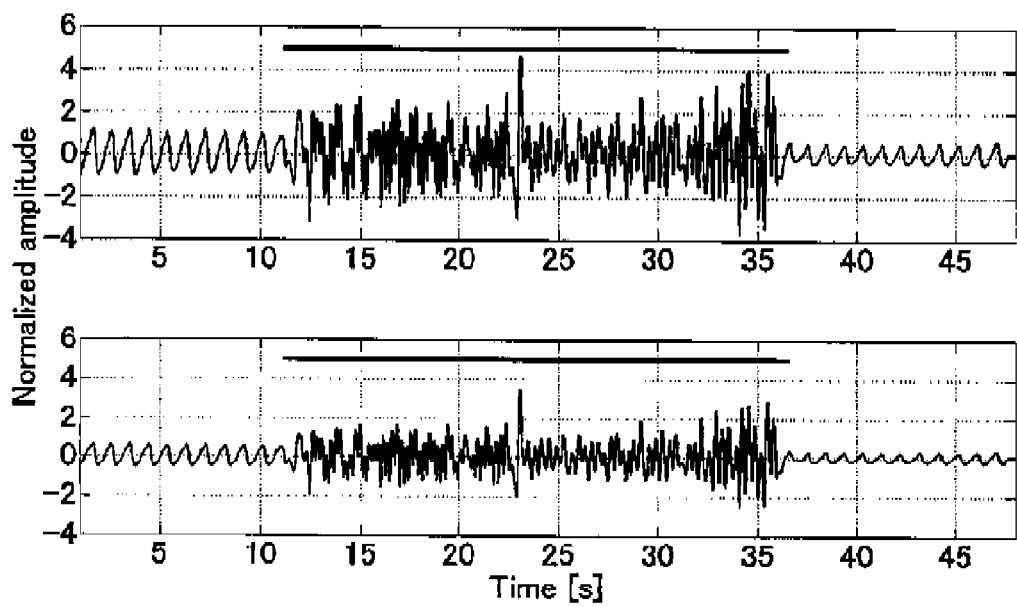
FIG. 3 shows observation signals which are measured by attaching a two-wavelength probe to a fingertip of a healthy male subject, and by artificially mixing an artifact.

FIG. 3 show observation signals which are measured by attaching a two-wavelength probe to a fingertip of a healthy male subject.

The upper portion of the figure shows an observation signal corresponding to the infrared light (IR), and the lower portion shows that corresponding to the red light (R).

The wavelengths are 940 nm (infrared light) and 660 nm (red light), respectively.

The solid line zones shown in the upper portions of the figures of FIG. 3 indicate a tapping zone where an artifact is artificially applied. In the tapping zone, a table surface is tapped with a fingertip on the side where the probe is attached, quickly (for example, about 3 Hz) and repeatedly.

In the example of FIG. 3, with respect to both the observation signals of the infrared light and the red light, a pulse wave is not seen in the artifact zone.

The observation signals are normalized by respective DC transmitted light components, and then filtered by a six-pole Butterworth filter having a bandwidth of 0.5 to 5 Hz. The sampling interval is 16 ms.

Figure 4:
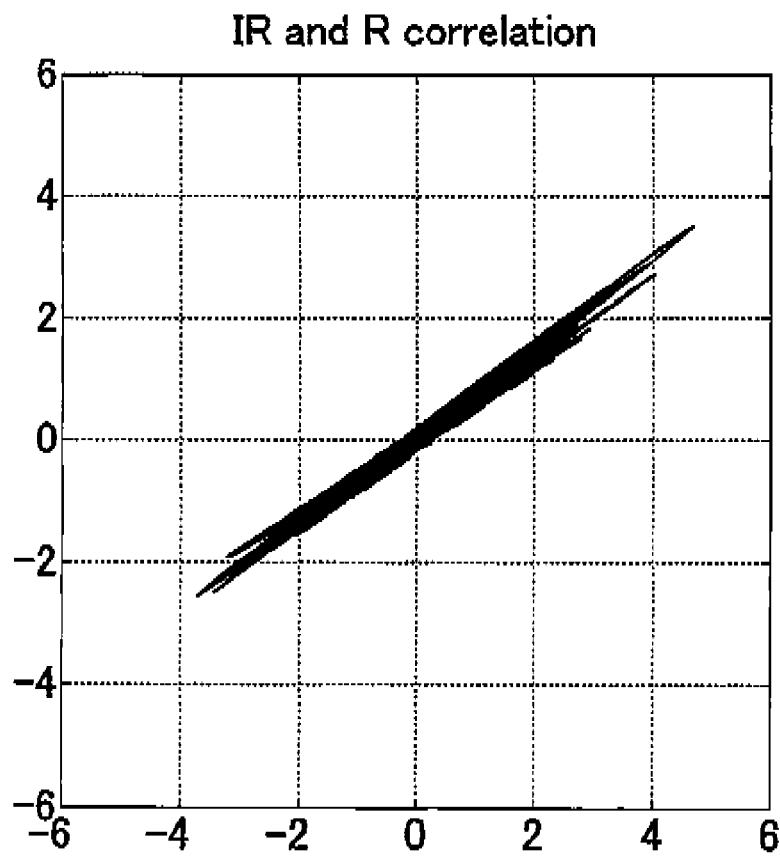
FIG. 4 is a correlation diagram of the infrared and red light observation signals shown in FIG. 3.

FIG. 4 is a correlation diagram of the infrared and red light observation signals shown in FIG. 3.

The abscissa indicates the infrared light, and the ordinate indicates the red light.

The gradient of FIG. 4 is given as a norm ratio of the infrared light to the red light in the artifact zone. From the gradient, the norm ratio "φN" of the artifact is known.

Next, a signal process of separating a pulse wave signal and noises (artifact signal) will be described with reference to FIG. 5.

Figure 5:
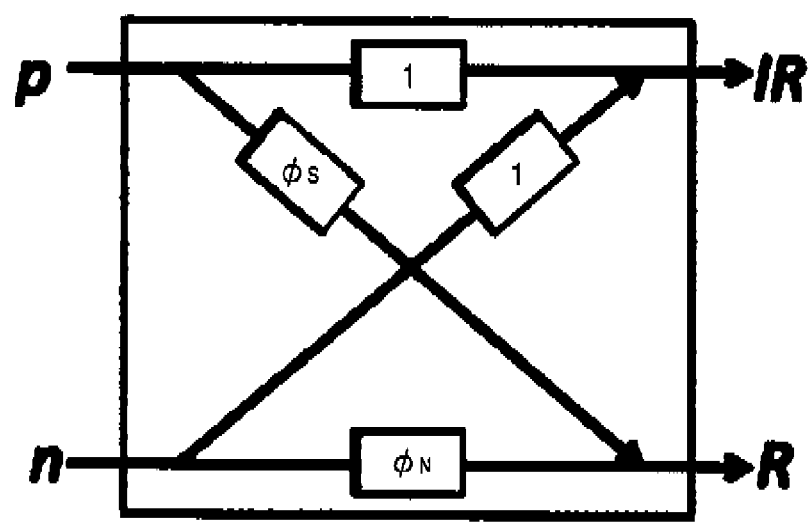
FIG. 5 is a diagram in which the example of FIG. 3 is modeled for the signal process.

FIG. 5 is a diagram in which the example of FIG. 3 is modeled for the signal process.

A pulse wave signal p at time tn is transmitted with a coefficient of 1 to an IR terminal, and transmitted with coefficient φS to an R terminal.

Similarly, an artifact signal n at time tn is transmitted with the coefficient of 1 to the IR terminal, and transmitted with coefficient φN to the R terminal.

The coefficient φS of the pulse wave signal is φS:=Rp, tn/IRp, tn, and the coefficient φN of the artifact signal is φN:=Rn, tn/IRn, tn.

When the observation time is prolonged to tn: tn+k, p, n, IR, and R are formed as vectors.

$$\phi_S := \|R_{pulse}\|_2 / \|IR_{pulse}\|_2 \qquad [\text{Exp. 1}]$$

$$\phi_N := \|R_{noise}\|_2 / \|IR_{noise}\|_2 \qquad [\text{Exp. 2}]$$

Hereinafter, it is assumed that a bold face indicates a vector.

A suffix "pulse" means the stable zone of the pulse wave, and a suffix "noise" means the artifact zone.

The stable zone of the pulse wave and the artifact zone are different both in time and zone length from each other.

$$\phi_S := \|R_{pulse}\|_2 / \|IR_{pulse}\|_2 \quad [\text{Exp. 1}]$$

$$\phi_N := \|R_{noise}\|_2 / \|IR_{noise}\|_2 \quad [\text{Exp. 2}]$$

Next, FIGS. 6A 6B, and 6C show results of three kinds of simulations which were performed while changing the relationships between the amplitudes of the pulse wave signal (pulse) and the artifact signal (Artifact).

In FIGS. 6A, 6B, and 6C, the abscissa indicates the IR signal, and the ordinate indicates the R signal.

In the simulations, the pulse wave was set to have a sawtooth waveform, and the artifact to have a sinusoidal waveform.

With respect to the relationships between the amplitudes of the pulse wave signal and the artifact signal, in FIG. 6A, the amplitudes of the pulse wave signal (pulse) and the artifact signal (Artifact) are (0.25:0.75).

In FIG. 6B, the amplitudes of the pulse wave signal (pulse) and the artifact signal (Artifact) are (0.33:0.66).

In FIG. 6C, the amplitudes of the pulse wave signal (pulse) and the artifact signal (Artifact) are (0.5:0.5).

When the norm ratio $\phi S$ indicated by Exp. 1 is $\phi S=0.55$, is the true value of the norm ratio indicated by Exp. 2 above:

$$\phi_N^{true} \quad [\text{Exp. 3}]$$

is 1.

All of the correlation diagrams shown in FIGS. 6A to 6C have a shape of a parallelogram. When artifact>pulse wave, the gradient of the short side coincides with $\phi S$, and that of the long side coincides with $\phi N$.

By contrast, when artifact<pulse wave, the gradient of the long side coincides with $\phi S$, and that of the short side coincides with $\phi N$.

The broken lines in the correlation diagrams of FIGS. 6A to 6C indicate the gradient of "$\phi N$" which shows "norm ratio" of the observation signal, and the solid lines indicate the gradient of $$\phi_N^+ \quad [\text{Exp. 4}]$$

which is "compensated norm ratio" that is proposed as a reference example, and that will be described later.

The compensated norm ratio coincides with "true value of norm ratio":

$$\phi_N^{true} \quad [\text{Exp. 3}]$$

which indicates the gradient of the long side of the parallelogram.

It is seen that, as the amplitudes of the pulse wave and the artifact are closer to each other, the discrepancy between "norm ratio" and "true value of norm ratio" is gradually more increased.

Next, the separation between the pulse wave signal and the artifact signal by the norm ratio will be described.

An observation signal $[IR\ R]^T$ is separated by a separation matrix S into a pulse wave signal vector p and an artifact signal vector n.

"T" in the shoulder means transposition.

From Exp. (1) below, a mixing matrix M is determined when "$\phi S$" and "$\phi N$" are set.

The separation matrix S is an inverse matrix of M shown in Exp. (2).

Here, "$\phi S$" is the norm ratio of the observation signal in the stable zone of the pulse wave.

When remaining "$\phi N$" can be estimated, M in which $[1\ \phi S]^T$ and $[1\ \phi N]^T$ are base vectors is determined.

$S = M^{-1}$ in which $$S = (M^T M)^{-1} M^T \quad [\text{Exp. 5}]$$

may be used.

In the above, "$\phi N$" is the norm ratio of the observation signal in the artifact zone.

It is assumed that "$\phi Npulse$"=1 in the stable zone of the pulse wave.

[Exp. 6]

$$M = \begin{bmatrix} 1 & 1 \\ \phi_S & \phi_N \end{bmatrix} \quad (1)$$

$$S = (M^T M)^{-1} M^T \quad (2)$$

$$[p\ n]^T = S[IR\ R]^T \quad (3)$$

In the above expressions, $\|\ \|2$ means a two-dimensional Euclidean norm. Suffixes pulse=t1:1+n and noise=tj:j+k indicate the stable zone of the pulse wave, and the artifact zone, respectively.

The time and the sample number are different in the stable zone of the pulse wave, and the artifact zone.

The configuration where "$\phi S$" and "$\phi N$" are obtained from the norm ratio is advantageous in that, because of the definition of the Euclidean norm, it is firm against sporadic noises.

The observation signal is a composite vector of a pulse wave vector and artifact vector which are different in gradient from each other.

Because the pulse wave is superimposed also in the artifact zone, therefore, $$\phi_N := \|R_{noise}\|_2 / \|IR_{noise}\|_2 \quad [\text{Exp. 2}]$$

and $$\phi_N^{true} \quad [\text{Exp. 3}]$$

which is the true value of the norm ratio are discrepant from each other.

As a reference example, therefore, there is a method in which "compensated norm ratio"

$$\phi_N^+ \quad [\text{Exp. 4}]$$

is used as means for correcting the discrepancy.

The compensation method is based on that the amplitude of the pulse wave superimposed in the artifact zone is equal to that in the stable zone.

The compensation is performed by following Exp. (4).

$$\phi_N^+ \quad [\text{Exp. 4}]$$

is referred to as "compensated norm ratio" of the artifact zone, and "$\phi N$" is referred to as the norm ratio of the zone.

In the artifact zone, it is often that the pulse wave signal is buried and hardly observed.

The norm is taken in the stable zone of the pulse wave signal, and $$\|IR_{pulse}\|_2 \text{ and } \|R_{pulse}\|_2 \quad [\text{Exp. 7}]$$

is set as the pulse wave amplitude.

The amplitude of the artifact signal is the norm of the artifact zone:

$$\|IR_{noise}\|_2 \text{ and } \|R_{noise}\|_2 \quad [\text{Exp. 8}]$$

Here, the sample number of the pulse wave zone is different from that of the artifact zone, and hence the norms are divided by the square root of the sample number of the respective zone.

An absolute value is used in view of that the value in the root sign is caused to become negative by observation noises other than the artifact.

[Exp. 9]

$$\overline{\|IR_{pulse}\|_2} := \frac{\|IR_{pulse}\|_2}{\sqrt{N_{pulse}}}$$

$$\overline{\|IR_{noise}\|_2} := \frac{\|IR_{noise}\|_2}{\sqrt{N_{noise}}}$$

$$\overline{\|R_{pulse}\|_2} := \frac{\|R_{pulse}\|_2}{\sqrt{N_{pulse}}}$$

$$\overline{\|R_{noise}\|_2} := \frac{\|R_{noise}\|_2}{\sqrt{N_{noise}}}$$

$$\phi_N^+ = \sqrt{\left|\frac{(\overline{\|R_{noise}\|_2})^2 - (\overline{\|R_{pulse}\|_2})^2}{(\overline{\|IR_{noise}\|_2})^2 - (\overline{\|IR_{pulse}\|_2})^2}\right|} \quad (4)$$

where $$(\overline{\|IR_{noise}\|_2})^2 \neq (\overline{\|IR_{pulse}\|_2})^2$$

A result of the separation in which the observation signal is separated by the separation matrix S with using "compensated norm ratio" that is the reference example will be described with reference to FIGS. 7A and 7B.

FIGS. 7A and 7B are views showing a waveform which is obtained by separating the observation signal by the separation matrix S.

In FIGS. 7A and 7B, the sampling interval is 16 ms, and a six-pole Butterworth filter having a bandwidth of 0.5 to 5 Hz is used.

The horizontal lines above the waveforms in FIGS. 7A and 7B indicate the artifact zone.

FIG. 7A shows the pulse wave which is separated by "norm ratio" and "φS", and FIG. 78 shows the pulse wave which is separated by above-mentioned "compensated norm ratio" and "φS".

In the former, needle-like large-amplitude artifacts are prominent.

In the latter, the pulse wave can be clearly seen, and, particularly at 20 seconds or later, the pulse wave is more clearly separated.

By contrast, in the zone of 12.5 to 18.5 seconds, the artifact is increased.

Figure 8A:
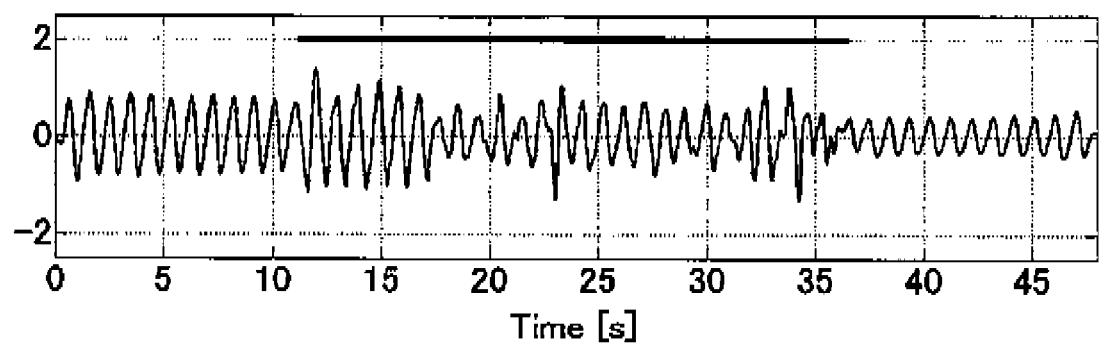
FIGS. 8A and 8B are views showing results of processes in which pulse waves that are obtained by separating the observation signals of FIG. 3 by the separation matrix S are further subjected to a 17-point moving average process.
Figure 8B:
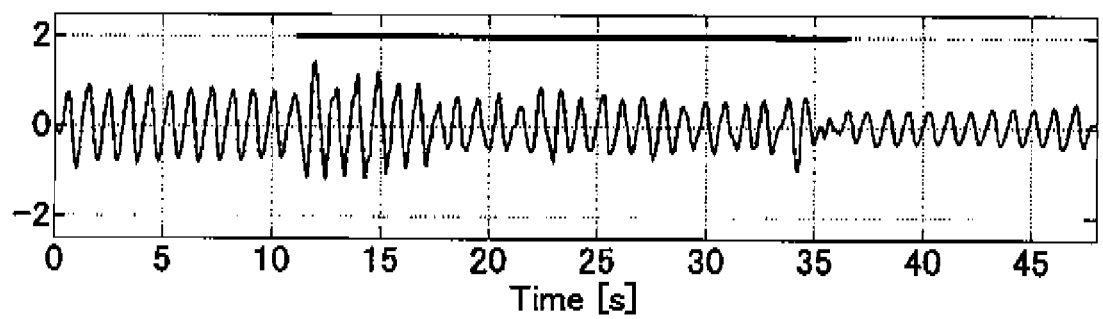

FIGS. 8A and 8B are views showing results of processes in which pulse waves that are obtained by separating the observation signals of FIG. 3 by the separation matrix S are further subjected to a 17-point moving average process in the artifact zone.

FIG. 8A shows the pulse wave which is separated by "norm ratio" and "φS", and FIG. 8B shows the pulse wave which is separated by above-mentioned "compensated norm ratio" and "φS".

It is seen that, in the separation by "compensated norm ratio", needle-like large-amplitude artifacts are reduced as compared with the separation by the norm ratio "φN".

In the separation by "compensated norm ratio", in the zone of 17 to 23 seconds, the artifact is reduced, and the pulse wave exhibits a smooth shape. Also in the zone of 30 to 35 seconds, because of the separation by "compensated norm ratio", the pulse wave exhibits a smooth shape.

It is considered that the pulse wave and the artifact are independent from each other. When the separation is adequately performed, therefore, the correlation diagram becomes close to a quadrangle or a rectangle.

FIGS. 9A to 9D are views showing correlations after separation.

Figure 9A:
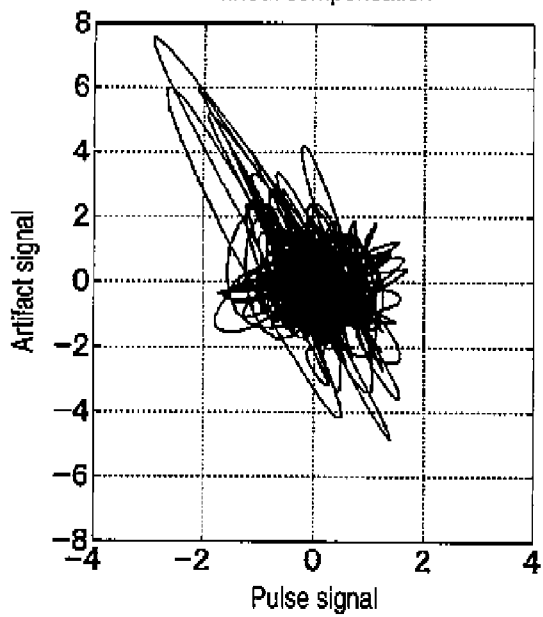
FIGS. 9A to 9D are views showing correlations after separation.
Figure 9B:
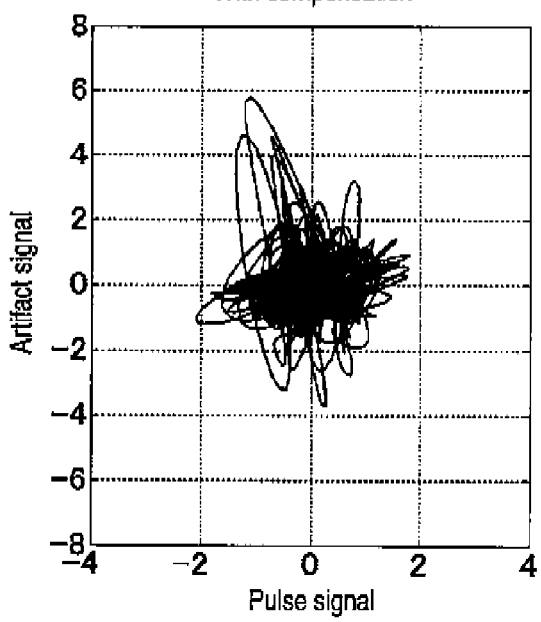
Figure 9C:
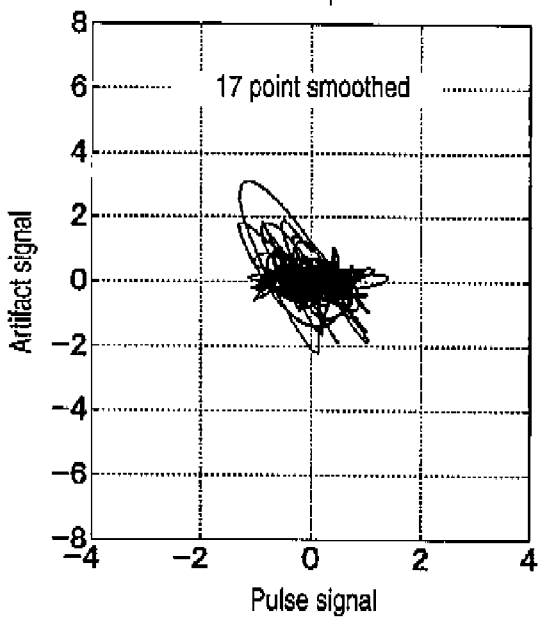
Figure 9D:
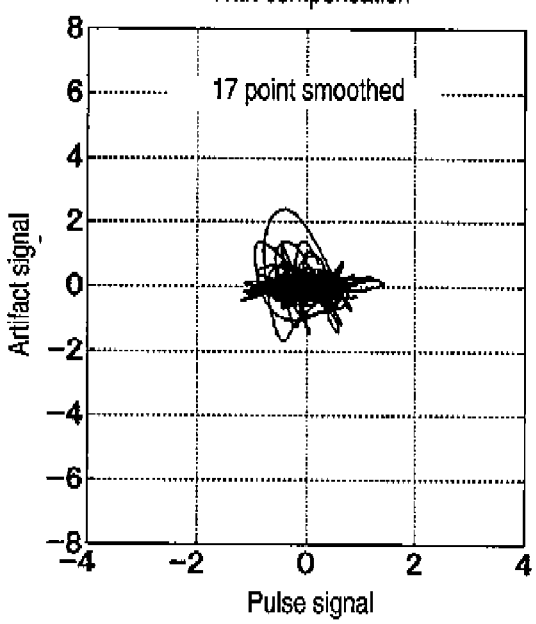

FIG. 9A shows correlations between a pulse wave which is separated by "norm ratio" and "φS" and the artifact, FIG. 9B shows correlations between a pulse wave which is separated by "compensated norm ratio" and "φS", and the artifact, FIG. 90 shows correlations between a pulse wave which is obtained by performing a 17-point moving average process on a pulse wave separated by "norm ratio" and "φS", and the artifact, and FIG. 9D shows correlations between a pulse wave which is obtained by performing a 17-point moving average process on a pulse wave separated by "compensated norm ratio" and "φS", and the artifact. It is seen that the case of FIG. 9B is separated more adequately than that of FIG. 9A, and the case of FIG. 9D is separated more adequately than that of FIG. 9C.

In observation, "true value of norm ratio" is unknown. Therefore, the degree of approach of "compensated norm ratio" to "true value of norm ratio" cannot be known.

Therefore, the result of separation by "compensated norm ratio" is evaluated with an evaluation function H of Exp. (6) below. In the expression, [Σ] means a variance-covariance matrix of the separated pulse wave signal vector p and the artifact signal vector n.

H is a ratio of absolute values of trace [Σ] and on-diagonal element $2\Sigma_{12}$.

When compensation is adequately performed, [Σ] approaches a diagonal matrix. As the value of H is smaller, the independences of p and n are higher.

[Exp. 10]

$$[\Sigma] := \begin{bmatrix} \Sigma_{11} & \Sigma_{12} \\ \Sigma_{21} & \Sigma_{22} \end{bmatrix} = [p\ n]^T [p\ n] \quad (5)$$

$$H := \frac{\left|2\Sigma_{12}\right|}{\mathrm{trace}[\Sigma]} \quad (6)$$

FIG. 10 shows results of evaluation of separation of the pulse wave and the artifact by the evaluation function H.

In FIG. 10, the upper row indicates the case where separation is performed by "norm ratio", and the lower row indicates the case where separation is performed by "compensated norm ratio".

In the both cases, evaluation results in the case of a six-pole Butterworth filter having a bandwidth of 0-5 to 5 Hz, and the case of a 17-point moving average process after the process of the filter are shown.

It is seen that, in the case where separation is performed by "compensated norm ratio", smaller values H=0.0042 and H=0.0492 are attained, and the diagonality is improved.

In the observation waveforms of FIG. 3 used in the description of "compensated norm ratio" which is the reference example, the artifact is artificially applied, and hence "compensated norm ratio" is a fixed value.

However, usually, an actual artifact is temporally changed. In such a case, also $$\phi_N^{true} \quad \text{[Exp. 3]}$$

which is "true value of norm ratio" is changed, but "compensated norm ratio":

$$\phi_N^+ \quad \text{[Exp. 4]}$$

is a fixed value, and cannot follow a change. Therefore, the quality of separation is lowered.

The invention is relates to a technique of improving the configuration where "compensated norm ratio" which is the reference example is not sufficient for an artifact that is temporally changed.

Therefore, the leak of an artifact into the pulse wave in the model of FIG. 5 will be discussed.

A true mixing matrix is assumed to be $$M^{true} \quad \text{[Exp. 11]}$$

and the inverse matrix thereof is assumed to be the separation matrix S.

[Exp. 12]

$$M^{true} = \begin{bmatrix} 1 & 1 \\ \phi_S^{true} & \phi_N^{true} \end{bmatrix}$$

$$M_{sep} = \begin{bmatrix} 1 & 1 \\ \phi_S & \phi_N \end{bmatrix}$$

$$S = (M_{sep}^T M_{sep})^{-1} M_{sep}^T$$

$$[p \ n]^T = \overline{SM^{true}[p^{true} \ n^{true}]^T}^{=[IR \ R]^T}$$

$$= \begin{bmatrix} \left(\dfrac{\phi_N - \phi_S^{true}}{\phi_N - \phi_S}\right) & \left(\dfrac{\phi_N - \phi_N^{true}}{\phi_N - \phi_S}\right) \\ \left(\dfrac{\phi_S^{true} - \phi_S}{\phi_N - \phi_S}\right) & \left(\dfrac{\phi_N^{true} - \phi_S}{\phi_N - \phi_S}\right) \end{bmatrix}$$

$$[p^{true} \ n^{true}]^T$$

$$p = \left(\dfrac{\phi_N - \phi_S^{true}}{\phi_N - \phi_S}\right) p^{true} + \left(\dfrac{\phi_N - \phi_N^{true}}{\phi_N - \phi_S}\right) n^{true}$$

$$L = \dfrac{(\phi_N - \phi_N^{true}) n^{true}}{(\phi_N - \phi_S^{true}) p^{true}} \quad (7)$$

When the true mixing matrix:

$$M^{true} \quad \text{[Exp. 11]}$$

is different in parameter value from the separation matrix S, the artifact leaks into the pulse wave.

The leak ratio L can be evaluated by Exp. (7).

For example, the amplitudes of the pulse wave and the artifact are assumed to be 1, and the pulse wave and the artifact are mixed with each other by:

$$\phi_S^{true}=0.55, \phi_N^{true}=0.75 \quad \text{[Exp. 13]}$$

Thereafter, separation is performed by:

$$\phi_S 0.55, \phi_N=0.95 \times \phi_N^{true} \quad \text{[Exp. 14]}$$

When the discrepancy between "norm ratio" and "true norm ratio" is only 5%, then, 16% of the amplitude of the artifact leaks into the pulse wave. This leak is not small.

Usually, "true norm ratio" changes with time. By contrast, "compensated norm ratio" is fixed in the artifact zone, and cannot follow the temporal change of "true norm ratio". Therefore, any countermeasure is necessary.

As described above, the phenomenon where the pulse wave is superimposed also in the artifact zone causes "norm ratio" and "true norm ratio" to be discrepant from each other. According to the invention, consequently, "successively-compensated norm ratio":

$$S\phi_N^+ \quad \text{[Exp. 15]}$$

which will be described later is proposed as means for correcting the discrepancy.

The compensation method is premised on that the amplitude of the pulse wave superimposed in the artifact zone is equal to that of the pulse wave in the stable zone.

The compensation is successively performed at each sampling point according to Exp. (8) below. This expression:

$$S\phi_N^+(J) \quad \text{[Exp. 16]}$$

is referred to as the successively-compensated norm ratio at sample timing J of the artifact zone.

In the artifact zone, the pulse wave signal is buried in the artifact and hardly observed. The norm is taken in the stable zone of the pulse wave signal, and $$\overline{\|IR_{pulse}\|_2} \text{ and } \overline{\|R_{pulse}\|_2} \quad \text{[Exp. 17]}$$

are set as the pulse wave amplitude.

By contrast, considering J and preceding and succeeding k points, norms of (2k+1) points in total:

$$\overline{\|IR(J)_{J-k:J+k}\|_2} \text{ and } \overline{\|(J)_{J-k:J+k}\|_2} \quad \text{[Exp. 18]}$$

are set as the artifact amplitude at timing J.

Since the sample number of the pulse wave zone is different from that of the artifact zone, $$\overline{\|\cdot\|_2} \quad \text{[Exp. 19]}$$

is a value which is obtained by division with the square root of the sample number of the respective zone, i.e., $$\sqrt{N_{pulse}} \quad \text{[Exp. 20]}$$

in the case of the pulse wave, and $$\sqrt{2k+1}$$

in the case of the artifact. The absolute value is used in view of that the value in the root sign is caused to become negative by observation noises other than the artifact.

[Exp. 21]

$$\overline{\|IR_{pulse}\|_2} := \dfrac{\|IR_{pulse}\|_2}{\sqrt{N_{pulse}}}$$

$$\overline{\|IR(J)_{J-k:J+k}\|_2} := \dfrac{\|IR_{J-k:J+k}\|_2}{\sqrt{2k+1}}$$

$$\overline{\|R_{pulse}\|_2} := \dfrac{\|R_{pulse}\|_2}{\sqrt{N_{pulse}}}$$

$$\overline{\|R(J)_{J-k:J+k}\|_2} := \dfrac{\|R_{J-k:J+k}\|_2}{\sqrt{2k+1}}$$

$$S\phi_N^+(J) = \sqrt{\left|\dfrac{(\overline{\|R(J)_{J-k:J+k}\|_2})^2 - (\overline{\|R_{pulse}\|_2})^2}{(\overline{\|IR(J)_{J-k:J+k}\|_2})^2 - (\overline{\|IR_{pulse}\|_2})^2}\right|} \quad (8)$$

where $$(\overline{\|IR(J)_{J-k:J+k}\|_2})^2 \neq (\overline{\|IR_{J-k:J+k}\|_2})^2$$

Figure 11:
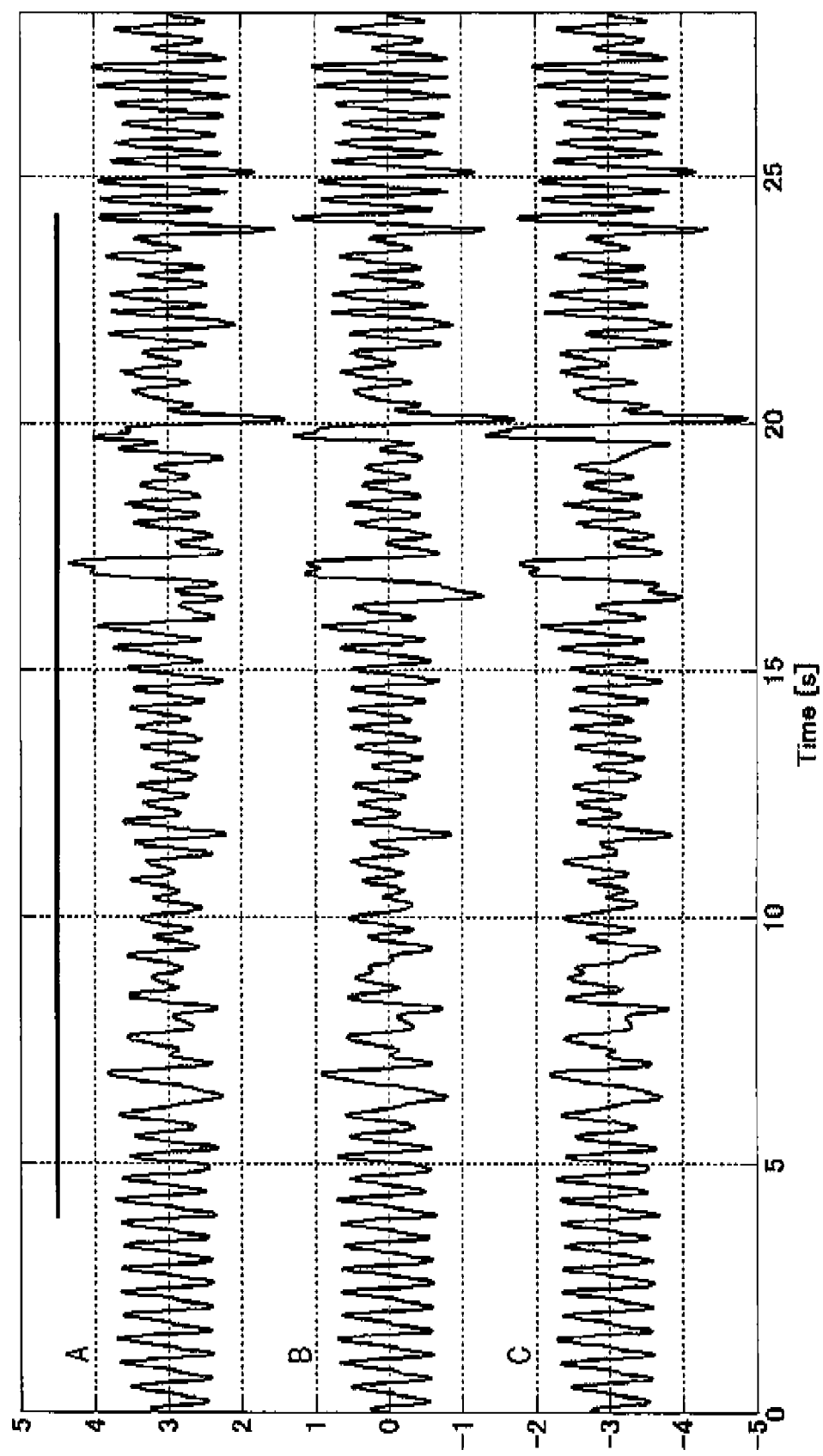
FIG. 11 is a view showing results of separation of the observation signal with using "successively-compensated norm ratio", "norm ratio", and "compensated norm ratio".

FIG. 11 shows results of separation of the observation signal by the separation matrix S with using "successively-compensated norm ratio" which is given by Exp. (8) above, together with results in the case where "norm ratio" and "compensated norm ratio" which is the reference example are used.

In FIG. 11, A shows the case where the artifact zone is separated by "successively-compensated norm ratio", B shows the case where the artifact zone is separated by "compensated norm ratio", and C shows the case where the artifact zone is separated by "norm ratio".

In FIG. 11, when the pulse waves in the zone of 5 to 20 seconds are compared with each other, the artifact amplitude in the separation by "successively-compensated norm ratio" in A is smaller than that in the cases of B and C.

In the vicinity of 20 seconds, particularly, there is a difference in amplitude, and, in the vicinity of 8 seconds, the pulse waves of B and C can be seen, but, in A, clear separation is performed as a pulse wave which is well connected to the preceding and succeeding portions.

In the base before the artifact in the vicinity of 17 seconds, the shape of the pulse wave is clearly separated as compared with B and C.

Furthermore, also in the steep rising portion of the artifact immediately before 20 seconds, the shape of the pulse wave is clearly separated as compared with B and C.

Figures 12, 13:
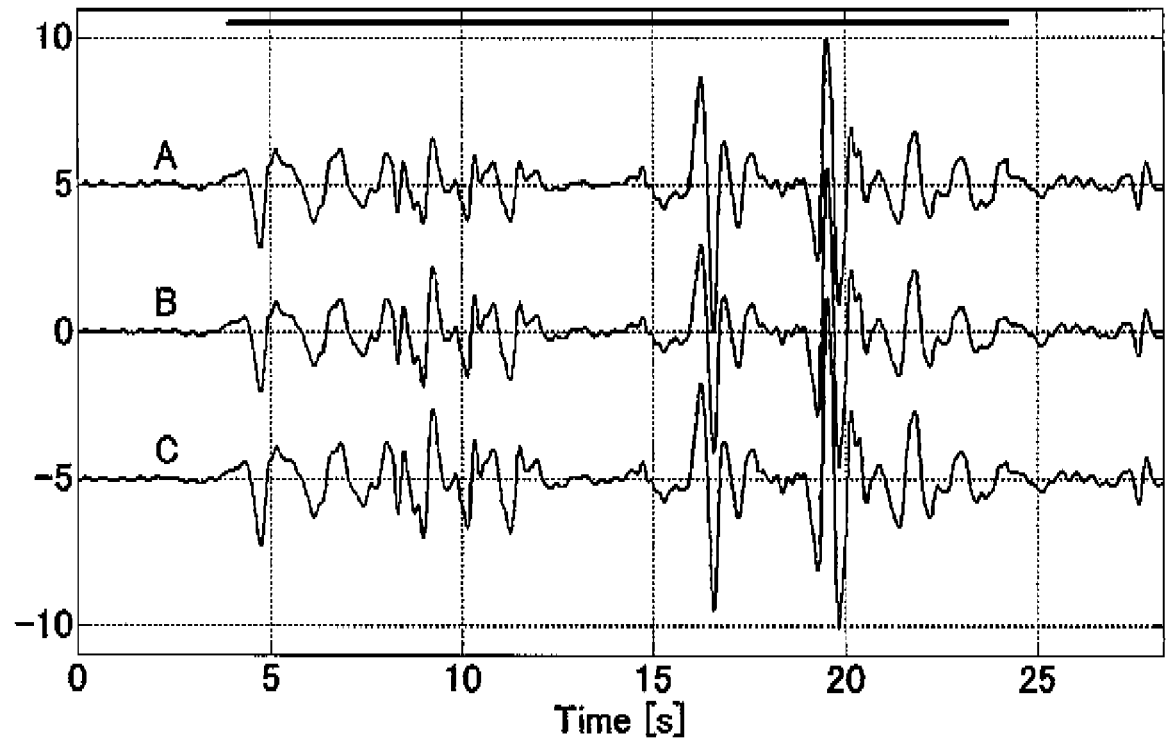
FIG. 12 is a view showing artifacts separated by separation methods due to "successively-compensated norm ratio", "norm ratio", and "compensated norm ratio".
FIG. 13 is a view showing results of evaluation by the evaluation function H.

FIG. 12 is a view showing artifacts separated by three kinds (A, B, and C) of separation methods.

From FIG. 12, it is seen that the artifact amplitude is separated in the sequence of C>B>A.

Therefore, it is seen that "successively-compensated norm ratio" in the invention can perform correction to a more adequate value and is superior as compared with "norm ratio" and "compensated norm ratio" which is the reference example.

In observation, "true value of norm ratio" is unknown. Therefore, the degree of approach of "compensated norm ratio" to "true value of norm ratio" cannot be known.

Therefore, the result of separation by "compensated norm ratio" is evaluated with the evaluation function H of Exp. (6) above. In the expression, [Σ] means a variance-covariance matrix of the separated pulse wave signal vector p and the artifact signal vector n.

H is a ratio of absolute values of trace [Σ] and on-diagonal element $2\Sigma_{12}$.

When compensation is adequately performed, [Σ] approaches a diagonal matrix. As the value of H is smaller, the independences of p and n are higher.

FIG. 13 shows results of the evaluation.

The results of the evaluation with the evaluation function H show that, as the value of H is smaller, the separation is performed more satisfactorily.

Also from the results of the evaluation with the evaluation function H, similarly with the results of FIG. 11, it is seen that the separation is performed in the sequence of C>B>A.

Furthermore, the separation matrix S is ill-conditioned depending on the value of "successively-compensated norm ratio":

$S\phi_N^+$ [Exp. 15]

and oscillation or spikes are sometimes generated.

The following invention relates to an improved technique for relaxing ill conditions of the separation matrix S.

Instability of Separation Matrix and Noise Magnification Coefficient (1) Unstable Zone In an inverse problem, as a general property, the solution is unstable when the separation matrix is ill-conditioned.

Figure 14A:
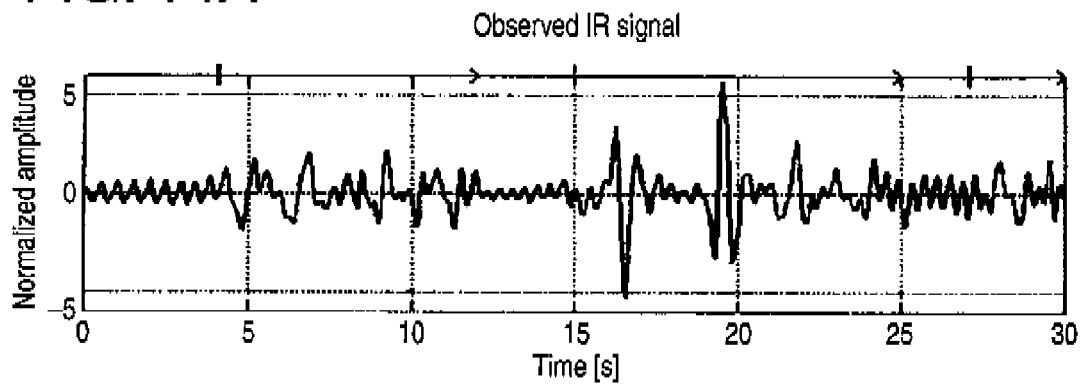
FIGS. 14A, 14B, and 14C are views showing a trend of a successive norm ratio at a sample number k=10 which is obtained from observation waveforms of IR and R.
Figure 14B:
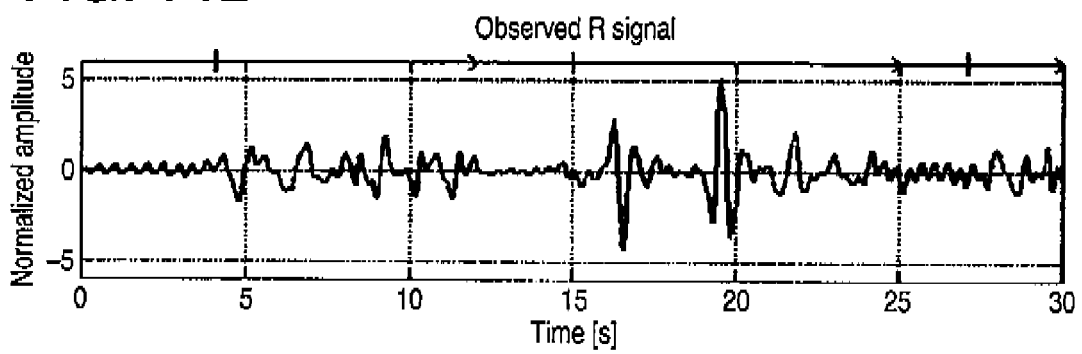
Figure 14C:
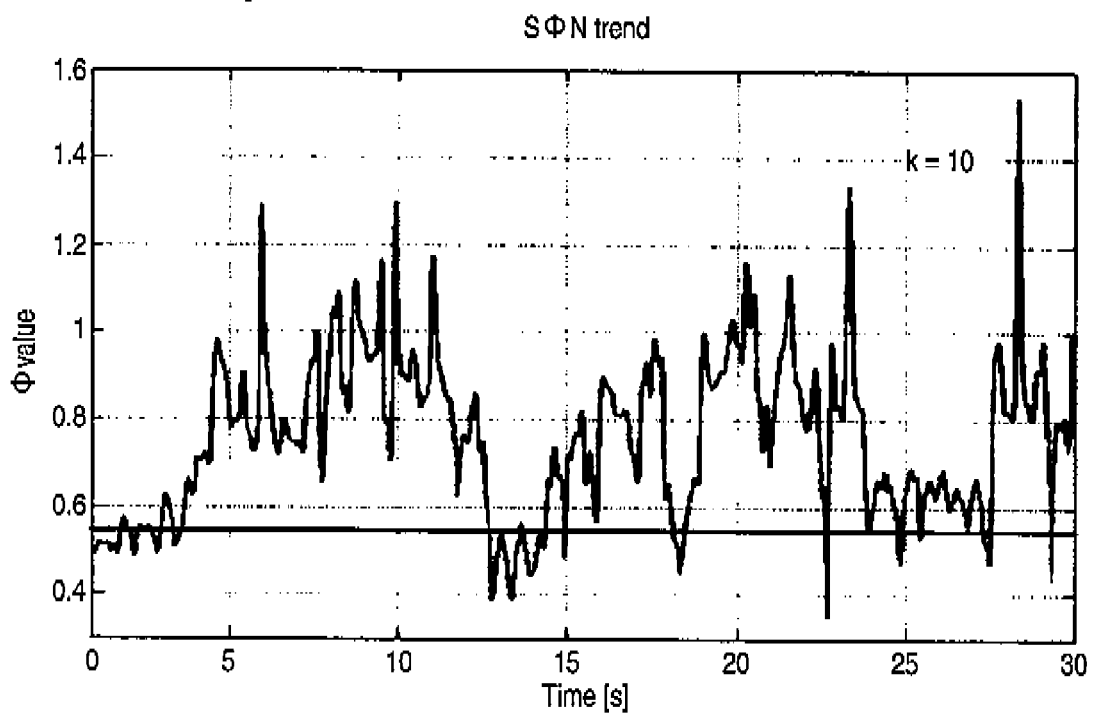

FIG. 14C shows a successive norm ratio S$\phi$N at the trend of $\phi$N in the case where the sample number k obtained from the observation waveforms shown in FIGS. 14A and 14B is k ~10.

As shown in FIG. 14C, the ratio of S$\phi$N is largely changed.

The horizontal line in FIG. 14C indicates $\phi$S which is obtained in the stable zone (1 to 3.5 seconds) of the pulse wave, and $\phi$S=0.5357.

The vicinities of intersections of the horizontal line and S$\phi$N are regions where S$\phi$N≡$\phi$S, the separation matrix is ill-conditioned, and oscillation or spikes are generated.

Usually, $\phi$S of a healthy person is about 0.55.

(2) Eigenvector and Eigenvalue of Separation Matrix

When observation noises exist in the observation signal, an abnormality such as that the amplitude is increased by separation sometimes occurs. Such an abnormality occurs in the case where the separation matrix is ill-conditioned, and the eigenvector and eigenvalue of the separation matrix are related to this.

In order to study ill conditions, the separation matrix S is assumed to be as Exp. (9):

[Exp. 22]

$$S = \frac{1}{\Delta}\begin{bmatrix} 1+\varepsilon & -1 \\ -1 & 1+\varepsilon \end{bmatrix} \quad (9)$$

here $$\Delta = (1+\varepsilon)^2 - 1$$

In the above expression, $\epsilon$ is a small value. Depending on the value of $\epsilon$, the separation matrix is changed from linear independent to linear dependent. When $\epsilon$>0, the column vector of S is linear independent, and, when $\epsilon$~0, the column vector is linear dependent and an ill-conditioned matrix.

When $\epsilon$≡0 is attained, an abnormality occurs.

In the case of two-wavelength SpO2, the separation matrix S is 2×2, and has two eigenvectors V and two eigenvalues λ.

In Exp. (10), G indicates a signal source vector such as a pulse wave, and O indicates an observation signal vector. The eigenvectors and eigenvalues of the separation matrix S are as indicated in Exp. (11) and Exp. (12). When the observation signal O is equal to the eigenvector V, Exp. (13) holds because of the relationship between the eigenvector and eigenvalue of a matrix. The norm of the separated signal source vector G is expressed by Exp, (14).

[Exp. 23]

$$G = S0 \quad (10)$$

$$V_1 = \frac{1}{\sqrt{2}}\begin{bmatrix} -1 \\ -1 \end{bmatrix}, V_2 = \frac{1}{\sqrt{2}}\begin{bmatrix} -1 \\ 1 \end{bmatrix} \quad (11)$$

$$\lambda_1 = \frac{1}{\varepsilon+2}, \lambda_2 = \frac{1}{\varepsilon} \quad (12)$$

$$G = SV = \lambda V \quad (13)$$

$$\|G_1\|_2 = \|\lambda_1 V_1\|_2 = \frac{1}{\varepsilon+2}, \quad (14)$$

$$\|G_2\|_2 = \|\lambda_2 V_2\|_2 = \frac{1}{\varepsilon}$$

When ϵ<1, λ has a large value.

Figure 15:
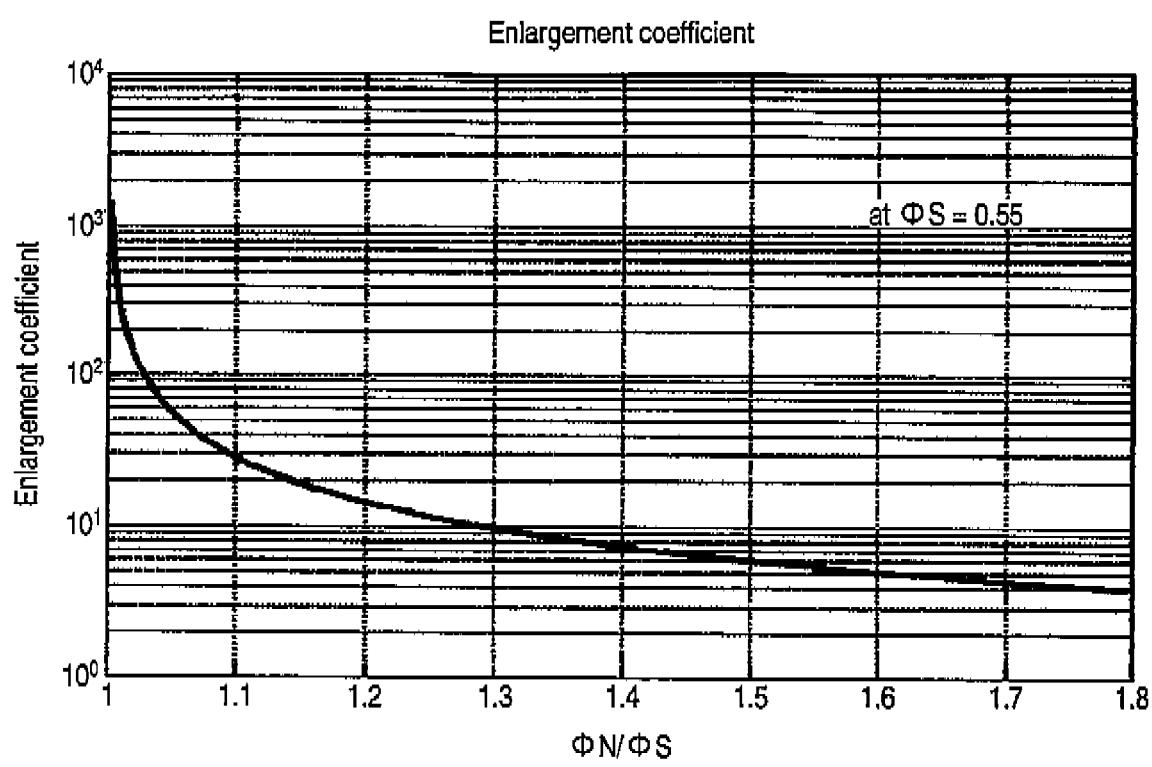
FIG. 15 is a view showing relationships between a noise magnification direction and a noise magnification coefficient.

FIG. 15 shows a noise magnification coefficient obtained from Exp. (14).

In the figure, φN is indicated by a ratio to φS, and φS is assumed to be 0.55. When φN/φS=1.2, the noise magnification coefficient is about 15 times over, when φN/φS=1.3, the noise magnification coefficient is about 10 times, and, when φN/φS=1, the noise magnification coefficient is infinite.

(3) Noise Magnification Direction and Noise Magnification Coefficient

The noise magnification coefficient is shown in FIG. 15. Here, the noise magnification direction is checked. As noises of norm 1 to be applied to the observation signal, sin of an amplitude 1 is added to the IR observation signal, and cos is added to the R observation signal.

Figure 16A:
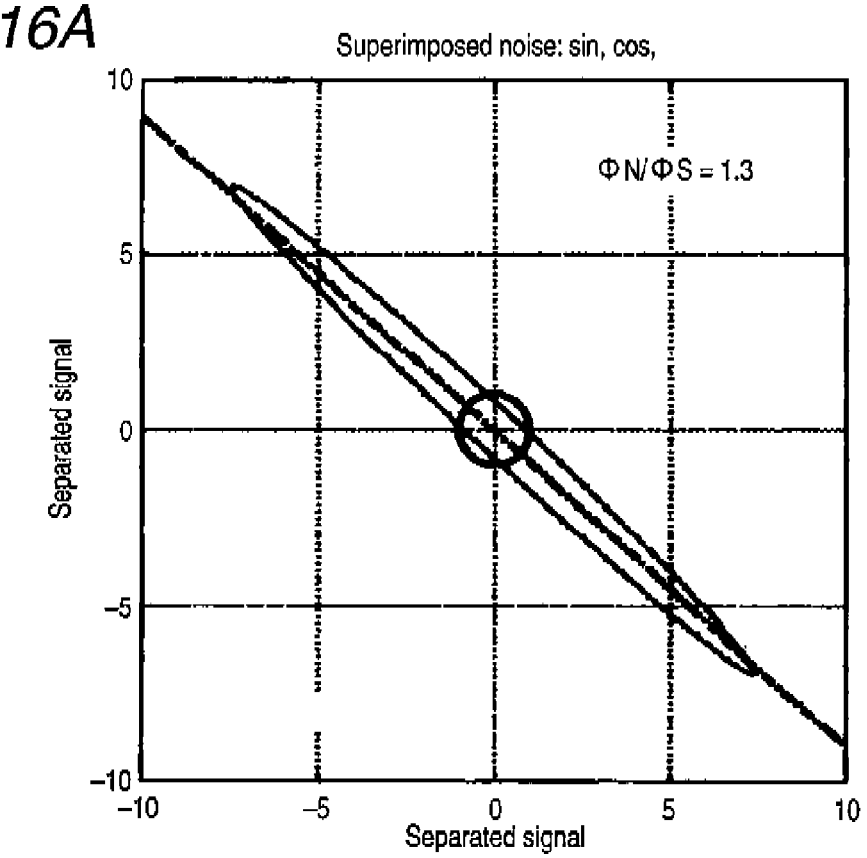
FIGS. 16A and 16B are views showing results of a simulation in which $\phi S$ and $\phi N$ of the separation matrix are set as $\phi S=0.55$ and $\phi N/\phi S=1.3$.
Figure 16B:
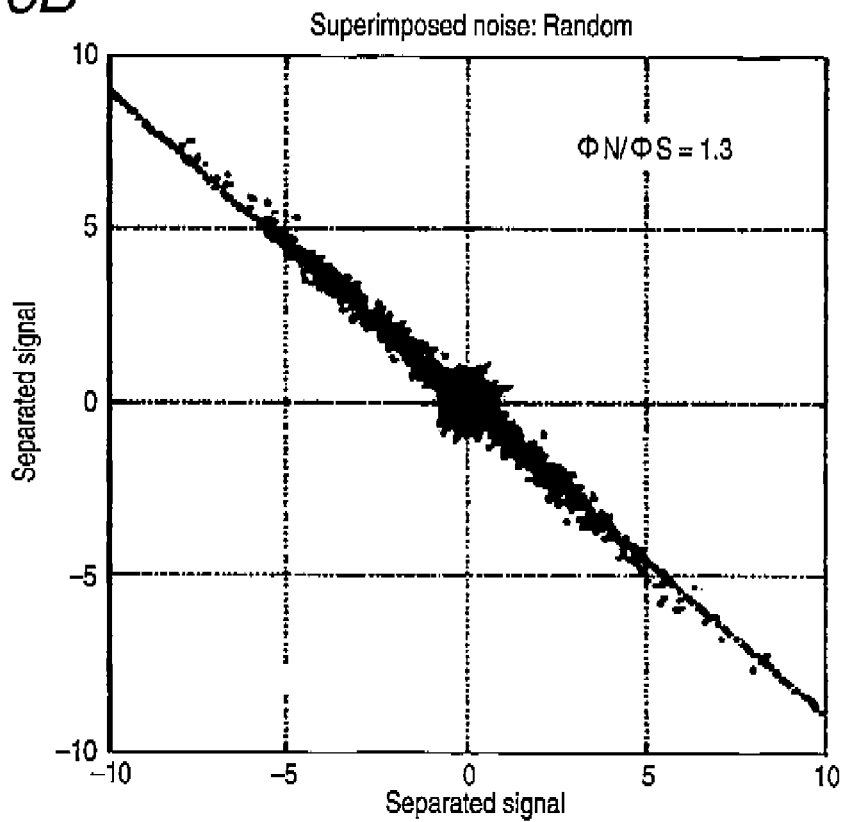

Independent random noise N(0, 1) is studied. FIGS. 16A and 16B show results of a simulation in which φS and φN of the separation matrix are set as φS=0.55 and φN/φS=1.3.

The circle at the center of FIG. 16A is a unit circle formed by sin and cos. The dashed line indicates the direction of the eigenvector of the separation matrix in the case where φN/φS=1.3.

The ellipse indicates the locus drawn by a separated signal which is obtained by separating the signal forming the unit circle with the separation matrix. The amplitude of the observation signal is increased in the direction of the eigenvector. The amplitude is indicated by the length between the apex of the long axis and the origin, and, when φN/φS=1.3, is about 10 times. In FIG. 15, when φN/φS=1.3, the magnification coefficient is about 10 times. Therefore, the results coincide with each other.

Similarly, the circular portion in FIG. 16B indicates the applied random noise. The peak amplitude forms a substantially circle. The dashed line indicates the eigenvector of the separation matrix. Also in the case of random noise, the noise magnification direction is maximum in the direction of the eigenvector of the separation matrix. When φN/φS=1.3, the noise magnification coefficient is about 10 times.

Relaxation of Ill Conditions by Gating (1) Flow of Processes

As a measure for relaxing ill conditions, gating is proposed.

Figure 17:
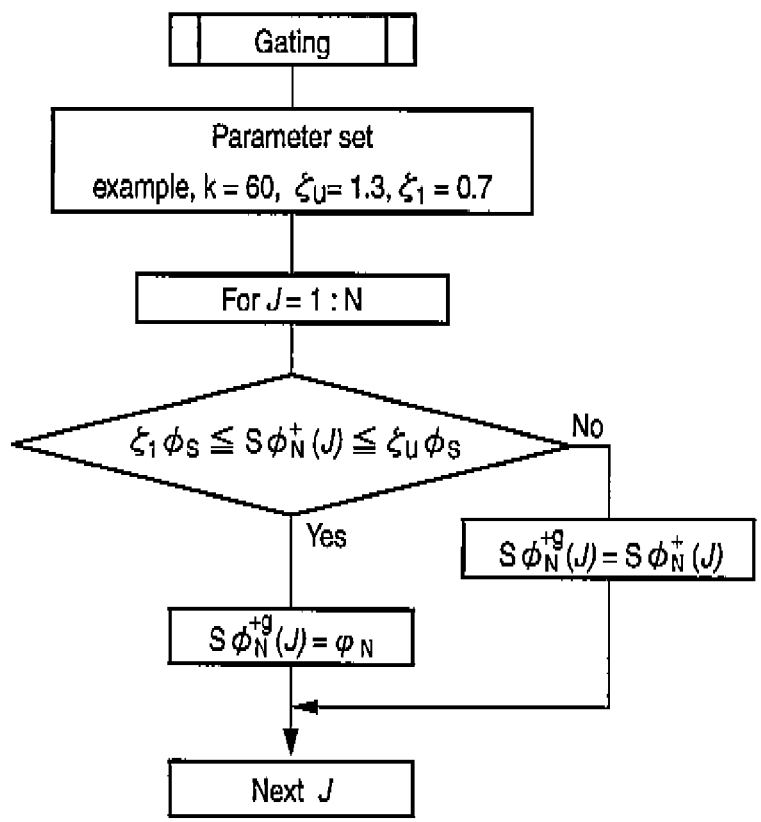
FIG. 17 is a chart showing the flow of processes of processing parameters related to the artifact.

FIG. 17 shows the flow of processes of processing parameters related to the artifact.

In gating, a gate is opened under ill conditions, and "successively-compensated norm ratio":

$S\phi_N^+$ [Exp. 15]

is replaced with $\phi_N$ [Exp. 32]

In the above, $\phi_N$ [Exp. 32]

is a value which is separate from φS, and which is previously determined.

The threshold for ill conditions is set by an upper limit $\xi_u$ and a lower limit $\xi_l$ of ξ. Here, ξ is a coefficient which multiplies φS by $\xi_u$ or $\xi_l$ times, and determined by FIG. 15.

For example, ξ is a coefficient in which $\xi_u$=1.3 and $\xi_l$=0.7, and which is symmetric about 1.

When $\xi_l \phi_S > S\phi_N^+(J) > \xi_u \phi_S$ [Exp. 24]

the parameter of the separation matrix is set to φS;

$S\phi_N^+$ [Exp. 15]

When $\xi_l \phi_S \leq S\phi_N^+(J) \leq \xi_u \phi_S$ [Exp. 30]

the parameter of the separation matrix is set to φS:

$\phi_N$ [Exp. 32]

Here, "gated successively-compensated norm ratio" is expressed by:

$S\phi_N^{+g}$ [Exp. 28]

(2) Selection of ξ

When ξ is selected to ξ=φN/φS=1.3, for example, the noise magnification coefficient is about 10. When the signal-to-noise ratio (SNR) of the observation signal is ensured to be 1/100 (−40 dB), the SNR after separation can be expected to be about 1/10 (−20 dB).

Magnifying observation noises constitute a vector directed toward the periphery of the direction of the eigenvector of the mixing matrix. When separated from the direction of the eigenvector, the noise magnification coefficient is reduced as indicated by the ellipse of FIG. 16A.

(3) Parameter Values Used in Stable Zone of Pulse Wave

When the gating is $\xi_l \phi_S \leq S\phi_N^+(J) \leq \xi_u \phi_S$ [Exp. 25]

the parameter of the separation matrix is set to φS;

$\phi_N$ [Exp. 32]

In bloodless tissue, φN is about 1. Therefore, $\phi_N$ [Exp. 32]

is set to 1.

When $\phi_N$ [Exp. 32]

is selected as to satisfy the following relationship, $\phi_N \gg \phi_S$, [Exp. 33]

the separation matrix is approximated by Exp. (15), and the pulse wave in the stable zone is projected as it is.

$$S = \frac{1}{(\varphi_N - \phi_S)} \begin{bmatrix} \varphi_N & -1 \\ -\phi_S & 1 \end{bmatrix}, \quad (15)$$

$$S \cong \begin{bmatrix} 1 & \frac{-1}{\varphi_N} \\ \frac{-\phi_S}{\varphi_N} & \frac{1}{\varphi_N} \end{bmatrix} \cong \begin{bmatrix} 1 & 0 \\ 0 & 0 \end{bmatrix}$$

Evaluation Function and Evaluation of Compensation

The "true value of norm ratio"

$\phi_N^{true}$ [Exp. 3]

is unknown.

Therefore, the degree that $S\phi_N^{+g}$ approaches to $\phi_N^{true}$ [Exp. 27]

is not known. Therefore, the result of separation by "gated successively-compensated norm ratio"

$S\phi_N^g$ [Exp. 28]

is evaluated by an evaluation function H of Exp. (20). In the expression, [Σ] means a variance-covariance matrix of the separated pulse wave signal vector p shown in Exp. (16) and the artifact signal vector n.

H is a ratio of absolute values of trace [Σ] and on-diagonal element $2\Sigma_{12}=2\Sigma_{21}$. When compensation is adequately performed, [Σ] approaches a diagonal matrix. As the value of H is smaller, the independences of p and n are higher, and the separation is more excellent.

[Exp. 29]

$$[\Sigma] := \begin{bmatrix} \Sigma_{11} & \Sigma_{12} \\ \Sigma_{21} & \Sigma_{22} \end{bmatrix} = [p\ n]^T[p\ n] \quad (16)$$

$$H := \frac{|2\Sigma_{12}|}{\text{trace}[\Sigma]} \quad (17)$$

FIGS. 18A to 18D show results of separation in which the pulse wave is separated from the waveforms in FIGS. 14A and 14B.

A symbol of | is drawn at the start point of an artifact zone, and that of > is drawn at the end point.

FIG. 18A shows a result of the case where separation is performed by "successively-compensated norm ratio"

$$S\phi_N^+ \quad [\text{Exp. 15}]$$

without conducting gating. In this case, k=10. In zones where ill conditions are caused, the amplitude is increased, and spikes are generated.

FIG. 18B shows a result of the case where separation is performed by "successively-compensated norm ratio"

$$S\phi_N^+ \quad [\text{Exp. 15}]$$

while the gating factors are set so that $\xi_u=1.3$, $\xi_1=0.7$, and k=10. In this case, spikes remain. Spikes are generated outside the thresholds $\xi_u>1.3$ and $\xi_1<0.7$. The residual spikes will be described later.

FIG. 18C shows a result of the case where separation is performed while the gating factors are set so that $\xi_u=1.3$, $\xi_1=0.7$, and k=60. In this case, spikes are not generated. In all of first, second, and third zones of the artifact, the artifact is greatly reduced by separation by the successively-compensated norm ratio. Without adjustment, the value of the evaluation function is H=0.0382.

FIG. 18D shows a result of the case where separation is performed by the norm ratio φN of the whole observation zone. The value of the evaluation function is H 0.2781.

Figure 19:
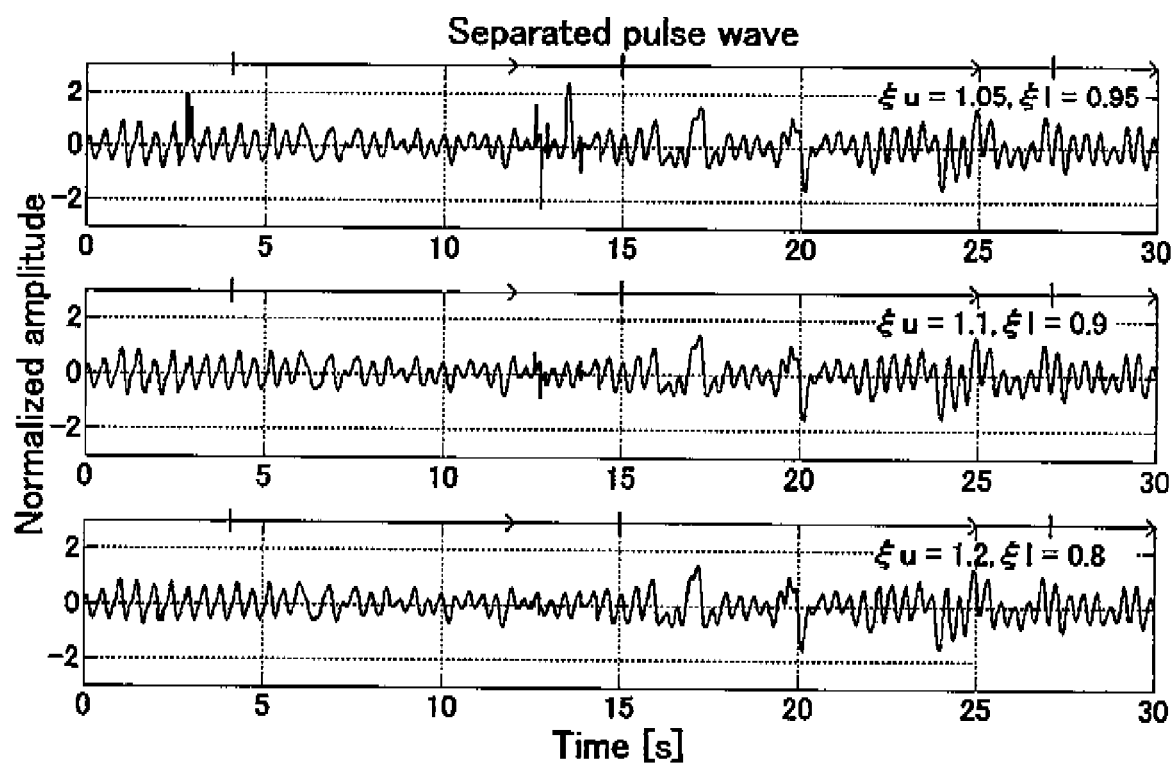
FIG. 19 is a view showing results of a process in which the pulse wave is separated with other parameters from the observation waveforms in FIGS. 14A and 14B.

FIG. 19 shows results of a process in which k=60 is set, gating is performed by three combinations of $\xi_u$ and $\xi_1$, and the pulse wave is separated.

It is seen that, when the interval between $\xi_u$ and $\xi_1$ is narrowed, spike are frequently generated. When $\xi_u=1.2$ and $\xi_1=0.8$, spikes are not generated.

When the threshold width is excessively increased, gating is frequently performed, and zones where adequate "successively-compensated norm ratio" is used are reduced. Therefore, the quality of separation is lowered.

Consideration of Residual Spikes

In FIG. 18B, even after gating, spikes remain in several places.

Therefore, the character of spikes in the vicinity of 6 seconds will be studied.

FIG. 20A to 20D show trends of the pulse wave between 5.7 to 6.2 seconds in FIG. 18B, and "gated successively-compensated norm ratio"

$$S\phi_N^{+g} \quad [\text{Exp. 28}]$$

In the figure, the time axis is expanded.

Figure 20A:
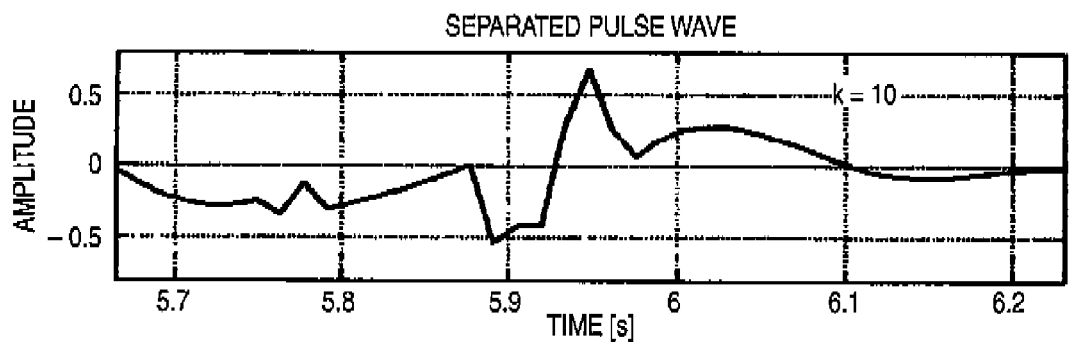
FIGS. 20A to 20D are views showing trends of the pulse wave and "gated successively-compensated norm ratio" while the time axis is expanded.

FIG. 20A shows the pulse wave which is separated by gating with k=10, and in which plural residual spikes exist before 5.8 seconds and in the vicinity of 5.9 seconds.

Figure 20B:
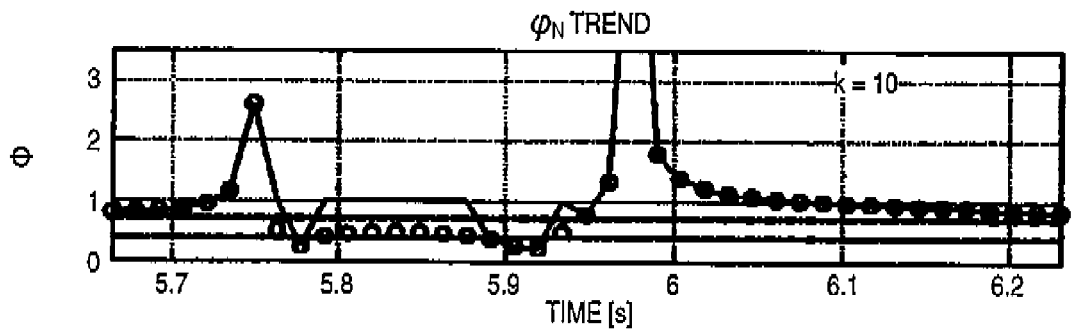

The solid line in FIG. 20B shows a trend of "gated successively-compensated norm ratio"

$$S\phi_N^{+g} \quad [\text{Exp. 28}]$$

on which gating has been performed. The symbols "○" indicate a trend of "successively-compensated norm ratio"

$$S\phi_N^+ \quad [\text{Exp. 15}]$$

on which gating has not been performed.

In the ordinate of the trend, an apex for displaying the vicinities of the thresholds is cut off.

The dashed lines indicate thresholds by which gating is performed. The thresholds are $\xi_u=1.3$ and $\xi_1=0.7$.

In the zones where the symbols "○" are within the thresholds (for example, from the vicinity of 5.8 seconds to before 5.9 seconds), gating is performed.

In gating, "gated successively-compensated norm ratio" is replaced with $$\phi_N \quad [\text{Exp. 32}]$$

which is previously determined in the zone.

The zone is shown by the straight-line portion of a value 1 which is in the vicinity of 5.8 to 5.9 seconds in FIG. 20B.

In places where the trend of "gated successively-compensated norm ratio" is outside the thresholds, residual spikes are generated a little before 5.8 seconds and in the vicinity of 5.9 seconds.

From the results, it is seen that gating is correctly performed within the thresholds which are designated by default.

Figure 20C:
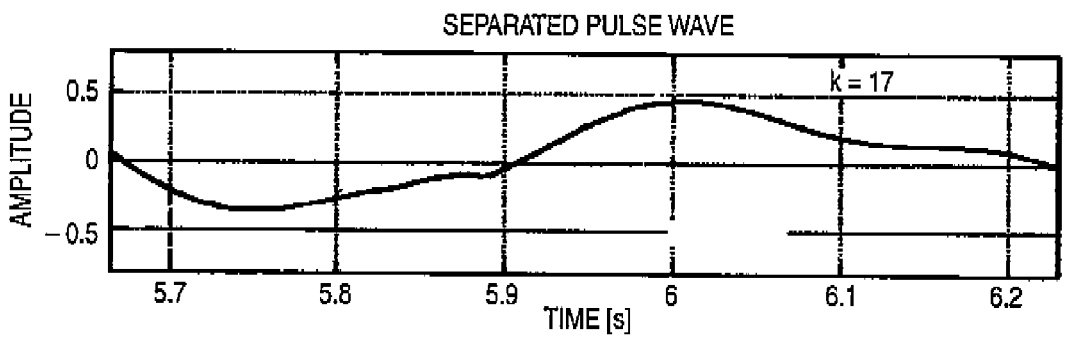

FIG. 20C shows the pulse wave which is separated with k=17. In the trend, spikes disappear.

Figure 20D:
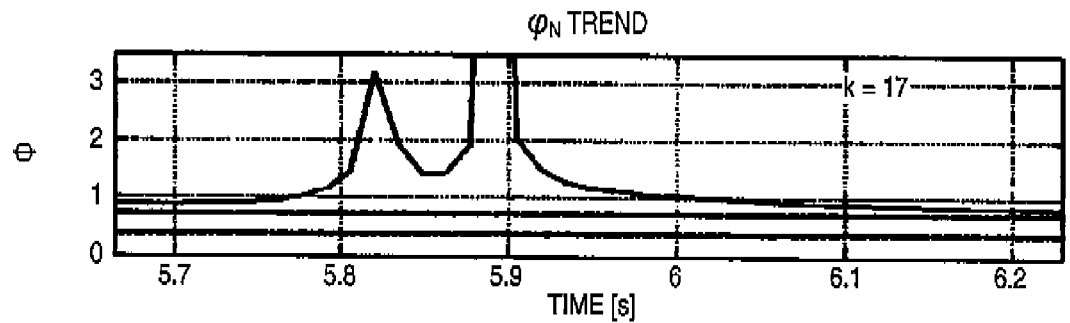

In FIG. 20D, the whole trend of "successively-compensated norm ratio" is above the thresholds, and hence gating is not performed.

Residual spikes are generated outside the thresholds which are designated by default. The spikes are generated by increase of the amplitude which is caused because the observation noise vector is in the same direction as the direction of the eigenvector of the separation matrix.

Relaxation of Ill Conditions by Regularization Parameter

As shown in Exp. (18), a regularization parameter is added as an additional term to the separation matrix, and λ which is an arbitrary small value is adjusted so that the value of the evaluation function is minimum. In determination of λ, recurrent calculation is required, and hence there is a disadvantage that it is difficult to adjust.

[Exp. 31]

$$S = \left(M^T M + \lambda^2 \begin{bmatrix} 1 & 0 \\ 0 & 1 \end{bmatrix}\right)^{-1} M^T \quad (18)$$

Figure 21A:
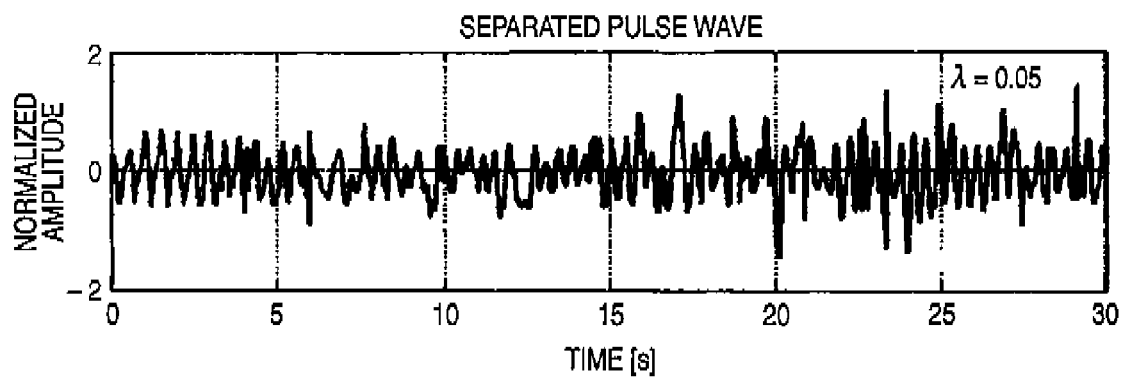
FIGS. 21A and 21B are views showing results of relaxation of ill conditions by a regularization parameter in the invention.
Figure 21B:
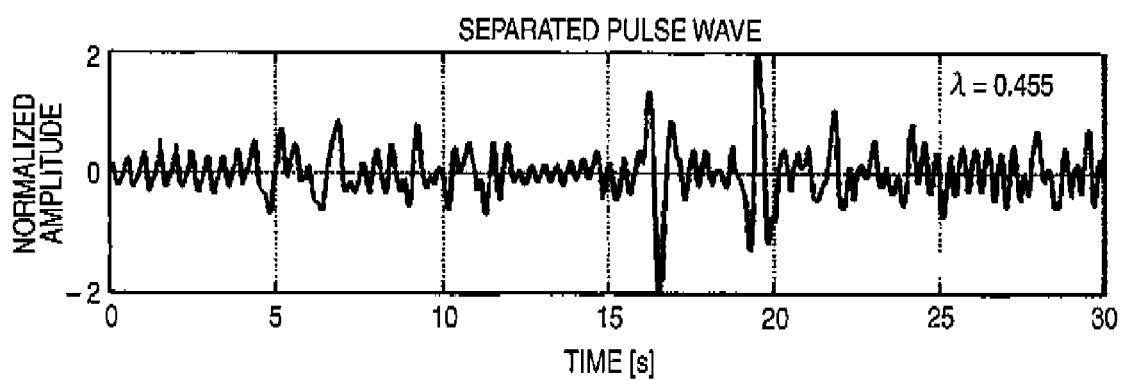

FIGS. 21A and 21B show results of the relaxation of ill conditions by the regularization parameter.

The observation waveforms of FIGS. 14A and 14B are used.

FIG. 21A shows an example in which ill conditions are relaxed with λ=0.05 and k=10. When λ=0.05, the value of the evaluation function is H=0.0042 or minimum. However, many spikes remain.

FIG. 21B shows an example in which ill conditions are relaxed with λ=0.465 and k=10. Spikes disappear, but the pulse wave is not well separated. The value of the evaluation function is H=0.888 or poor.

Example of Process of Pulse Wave Buried in Tapping Artifact

Figure 22A:
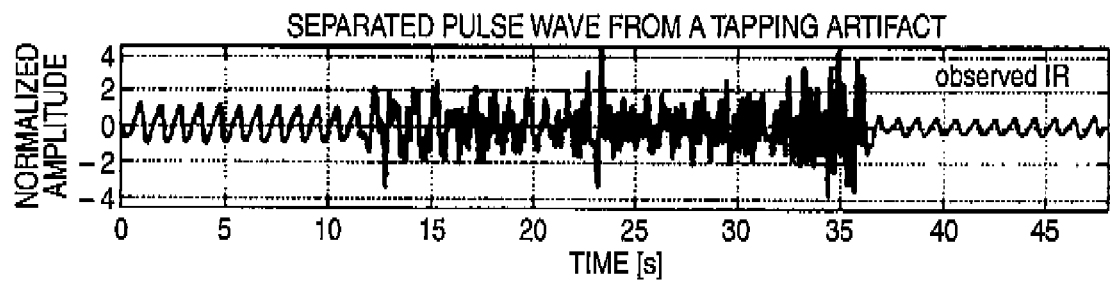
FIGS. 22A to 22C are views showing other process examples of a pulse wave which is buried in a tapping artifact.
Figure 22B:
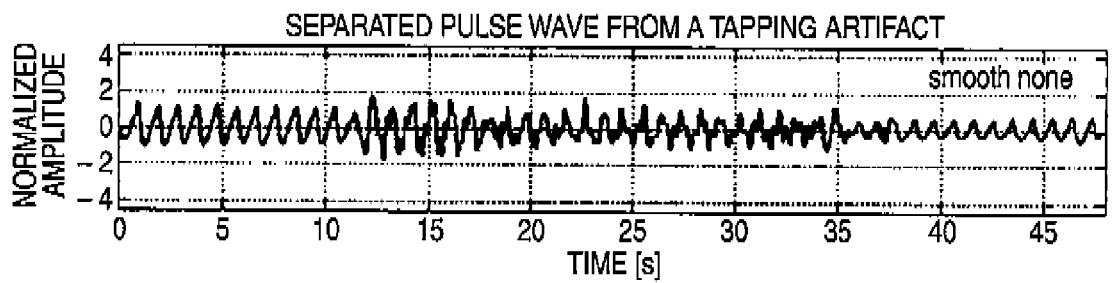
Figure 22C:
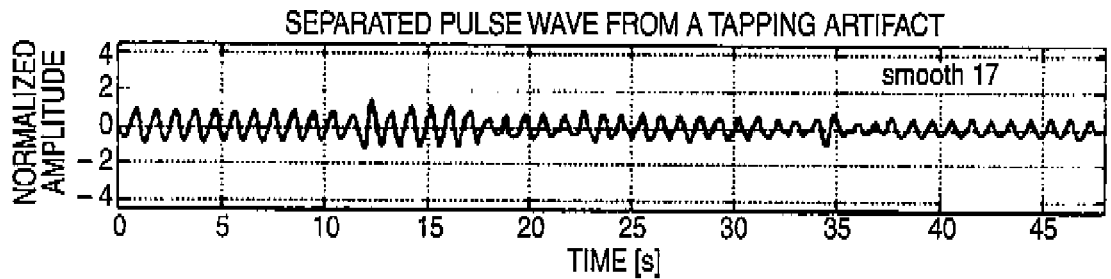

FIGS. 22A to 22C show examples in which the pulse wave that is buried in a tapping artifact is separated with using the same parameter as that in FIG. 18C which are the gating factors of k=60, $\lambda_u$=1.3, and $\xi_1$=0.7.

FIG. 22A shows an observation waveform of IR. The pulse wave image is buried in the artifact and hardly observed.

FIGS. 22B and 22C show a pulse wave which is separated by the successively-compensated norm ratio due to gating. In FIG. 22B, the pulse wave image is well separated in the tapping zone, and spikes are not generated. In FIG. 22C, a result of a 17-point moving average process in consideration of the cycle length of the pulse wave is shown. The pulse wave image is clearer than that of FIG. 22B. The value of the evaluation function is H=0.1302 and H=0.0253.

From the above description, it is obvious that the pulse wave can be separated by the successively-compensated norm ratio which performs the gating in the invention, without designating an artifact zone.

According to an aspect of the invention, it is possible to realize a signal processing method, signal processing apparatus, and pulse photometer using the same in which, even in the case where a large artifact such as motion of a hand or a foot, bitter sobbing, shiver, or cough is contained, a signal component can be separated more correctly.

What is claimed is:

1. A method of processing first and second signals obtained by measuring a medium, comprising:
    receiving the first and second signals corresponding to a respective first emitted light beam and second emitted light beam;
    separating vectors of the first and second signals by using a processor having a separation matrix into a vector of the pulse wave signal and a vector of the artifact signal, and outputting at least one of the vector of the pulse wave signal and the vector of the artifact signal, the separation matrix including a norm ratio of a stable zone of the pulse wave signal and a successively-compensated norm ratio of an artifact zone.

2. The method according to claim 1, wherein the successively-compensated norm ratio is obtained by the following expression:

$$\overline{\|IR_{pulse}\|_2} := \frac{\|IR_{pulse}\|_2}{\sqrt{N_{pulse}}}$$

$$\overline{\|IR(J)_{J-k:J+k}\|_2} := \frac{\|IR_{J-k:J+k}\|_2}{\sqrt{2k+1}}$$

$$\overline{\|R_{pulse}\|_2} := \frac{\|R_{pulse}\|_2}{\sqrt{N_{pulse}}}$$

$$\overline{\|R(J)_{J-k:J+k}\|_2} := \frac{\|R_{J-k:J+k}\|_2}{\sqrt{2k+1}}$$

$$S\phi_N^+(J) = \sqrt{\left|\frac{(\overline{\|R(J)_{J-k:J+k}\|_2})^2 - (\overline{\|R_{pulse}\|_2})^2}{(\overline{\|IR(J)_{J-k:J+k}\|_2})^2 - (\overline{\|IR_{pulse}\|_2})^2}\right|}$$

where $$(\overline{\|IR(J)_{J-k:J+k}\|_2})^2 \neq (\overline{\|IR_{J-k:J+k}\|_2})^2.$$

3. The method according to claim 2, wherein
    when the successively-compensated norm ratio satisfies a condition, the successively-compensated norm ratio is replaced with a prescribed value.

4. A biological signal processing apparatus comprising:
    a measuring unit configured to measure the first and second signals; and
    a processor configured to process the first and second signals according to the method of claim 1.

5. A pulse photometer including the biological signal processing apparatus according to claim 4, and configured to calculate at least one of an oxygen saturation of arterial blood, a dyshemoglobin concentration, and dye concentration injected in the blood, comprising:
    a light emitter configured to emit two light beams having different wavelengths, wherein the two light beams are transmitted through or reflected from living tissue corresponding to the medium;
    a light receiver configured to convert the two light beams into first and second electric signals,
    wherein the processor is also configured to remove a component of the artifact signal is by using the compensated norm ratio to obtain the pulse wave signal.

6. The pulse photometer according to claim 5, wherein
    the processor is further configured such that when the successively-compensated norm ratio satisfies a condition, the successively-compensated norm ratio is replaced with a value.

* * * * *